US008017115B2

(12) United States Patent
Irving et al.

(10) Patent No.: US 8,017,115 B2
(45) Date of Patent: Sep. 13, 2011

(54) THERAPEUTICAL USE OF ANTI-MYELIN ASSOCIATED GLYCOPROTEIN (MAG) ANTIBODIES

(75) Inventors: Elaine Alison Irving, Harlow (GB); Mary Vinson, Harlow (GB)

(73) Assignee: Glaxo Group Limited (GB)

( * ) Notice: Subject to any disclaimer, the term of this patent is extended or adjusted under 35 U.S.C. 154(b) by 733 days.

(21) Appl. No.: 10/550,363

(22) PCT Filed: Feb. 2, 2004

(86) PCT No.: PCT/EP2004/001016
§ 371 (c)(1),
(2), (4) Date: Apr. 15, 2007

(87) PCT Pub. No.: WO2004/083363
PCT Pub. Date: Sep. 30, 2004

(65) Prior Publication Data
US 2007/0269427 A1    Nov. 22, 2007

(30) Foreign Application Priority Data

Mar. 19, 2003  (GB) .................................. 0306309.6

(51) Int. Cl.
*A61K 39/395* (2006.01)
(52) U.S. Cl. ................ 424/133.1; 424/152.1; 424/177.1
(58) Field of Classification Search .................. None
See application file for complete search history.

(56) References Cited

U.S. PATENT DOCUMENTS

| 4,873,316 | A | 10/1989 | Meade et al. |
|---|---|---|---|
| 5,154,924 | A | 10/1992 | Friden |
| 5,182,107 | A | 1/1993 | Friden |
| 5,250,414 | A | 10/1993 | Schwab et al. |
| 5,527,527 | A | 6/1996 | Friden |
| 5,792,743 | A | 8/1998 | Schachner |
| 5,833,988 | A | 11/1998 | Friden |
| 5,932,542 | A | 8/1999 | Filbin |
| 6,203,792 | B1 | 3/2001 | Filbin |
| 6,399,577 | B1 | 6/2002 | Filbin |
| 6,548,061 | B1 | 4/2003 | Steeves et al. |
| 6,576,607 | B1 | 6/2003 | Schachner |
| 7,612,183 | B2 * | 11/2009 | Ellis et al. ............ 530/388.24 |
| 2004/0002790 | A1 | 1/2004 | Senn |
| 2004/0170627 | A1 | 9/2004 | Irving et al. |
| 2006/0165681 | A1 | 7/2006 | Ellis et al. |
| 2008/0014195 | A1 | 1/2008 | Irving et al. |

FOREIGN PATENT DOCUMENTS

| EP | 307434 A | 3/1989 |
|---|---|---|
| EP | 308434 B | 9/1993 |
| WO | WO96/16990 | 6/1996 |
| WO | 96/32959 | 10/1996 |
| WO | WO 97/01352 | 1/1997 |
| WO | WO 97/07810 | 3/1997 |
| WO | 98/12329 | 3/1998 |
| WO | 99/25378 | 5/1999 |
| WO | WO 99/53945 | 10/1999 |
| WO | WO99/58679 | 11/1999 |
| WO | 00/05364 | 2/2000 |
| WO | 00/31235 | 6/2000 |
| WO | 00/43039 | 7/2000 |
| WO | 00/63252 | 10/2000 |
| WO | 01/62907 | 8/2001 |
| WO | 02/062383 | * 8/2002 |

OTHER PUBLICATIONS

Paul, Fundamental Immunology, 1993, pp. 292-295.*
Padlan et al. (Proc Natl Acad Sci USA, 1989; 86:5938-5942).*
Chothia et al., Conformations of Immunoglobulin Hybervariable Regions, Nature 342:877-883 (1989).
Debellard et al., Myelin-Associated Glycoprotein Inhibits Axonal Regeneration from a Variety opf Neurons via Interaction with a Sialoglycoprotein, Molecular and Cellular Neuroscience 7:89-101 (1996).
Irving et al., Rapid Alteration of Tau in Oligodendrocytes afer Focal Ischemic Injury in the Rat: Involvement of Free Radicals, J. of Cerebral Blood Flow & Metabolism 17:612-622 (1997).
Lassmann et al., Dying-Back Oligodendrogliopathy: A Late Sequel of Myelin-Associated Glycoprotein Deficiency, GLIA 19:104-110 (1997).
Niederost et al., Nogo-A and Myelin-Associated Glycoprotein Mediate Neurite Growth inhibition by Antagonistic Regulation of RhoA and Rac1, J. of Neuroscience 22(23):10368-10376 (2002).
Poltorak et al., Myelin-Associated Glycoprotein, a Member of the L2/HNK-1 Family of Neural Cell Adhesion Molecules, Is Involvd in Neuron-Oligodendrocyte and Oligodendrocyte-Oligodendrocyte Interaction, J. of Cell Biology 105:1893-1899 (1987).
Tang et al., Soluble Myelin-Associated Glycoprotein (MAG) Found in Vivo Inhibits Axonal Regeneration, Molecular and Cellular Neuroscience 9:333-346 (1997).
Torigoe et al., Selective Inhibition of Early Axonal Regeneration by Myelin-Associated Glycoprotein, Experimetnal Neurology 150:254-262 (1998).
Umemori et al., Initial events of myelination involve Fyn tyrosine kinase signaling, Nature 367:572-576 (1994).
Valeriani et al., Quantitative Assessment of Ischemic Pathology in Axons, Oligodendrocytes, and Neurons: Attenuation of Damage After Transient Ischemia, J. of Cerebral Blood Flow & Metabolism 20:765-771 (2000).
Angal, et al., Mol. Immunol, 1993, vol. 30, pp. 105-108.
Beattie, et al. neuron, 2002, vol. 36, pp. 375-386.
Bickel, et al. Proc Natl. Acad. Sci. USA, 1993, vol. 90, pp. 2618-2622.
Broadwell, et al. Exp. Neurol., 1996, vol. 142, pp. 47-65.
Crowe, et al., Nature Medicine, 1997, vol. 3, pp. 73-76.
Dehouck, et al., J. Cell Biol., 1997, pp. 877-889.
Descamps, et al., Am. J. Physiol., 1996, vol. 270, H1149-H1158.

(Continued)

*Primary Examiner* — Daniel E Kolker
(74) *Attorney, Agent, or Firm* — Jason C. Fedon; William T. Han

(57) ABSTRACT

A method of promoting oligodendrocyte survival in a human suffering from, or at risk of developing, stroke or other neurological diseases utilizes anti-MAG antibodies or functional fragments of such antibodies.

9 Claims, 8 Drawing Sheets

OTHER PUBLICATIONS

Duffy, et al. Brain Res., 1987, vol. 420, pp. 32-38.
Duncan, A. R.; Woolf, J.M.; Partridge, L.J.; Burton, D.R.; Winter, G. Localization of the binding site for the human high-affinity Fc receptor on IgG. Nature, 1988, vol. 332. 563-564.
Duncan, A.R.; Winter, G. The binding site for C1q on IgG. Nature, 1988, vol. 332, pp. 738-740.
Friden, et al., J. Pharm. Exp. Ther., 1996, vol. 278, pp. 1491-1498.
Green L.L. J Immunol Methods, Dec. 10, 1999, vol. 231, pp. 11-23.
Irving, et al., Acta Neuropathol (Berl), 2001, vol. 102, pp. 627-635.
Kabat, et al., Sequences of Proteins of Immunological interest. U.S. Department of Health and Human Services, National Institutes of Health, 1987, Table of contents only.
Pardridge, et al. Pharm. Res., 1995, vol. 12, pp. 807-816.
Queen, et al., Proc. Natl. Acad. Sci. USA, 1989, vol. 86, pp. 10029-10032.
Roher, et al., Biochemistry, 2002, vol. 41, pp. 11080-11090.
Rouselle, et al., Mol. Pharm., 2000, vol. 57, pp. 679-686.
Rouselle, et al., Journal of Pharmacology and Experimental Therapeutics, 2001, vol. 296, pp. 124-131.
Saito, et al., Proc. Natl. Sci. USA, 1995, vol. 92, pp. 10227-10231.
Sambrook, et al., Molecular Cloning (A Laboratory Manual. Cold Spring Harbor Laboratory, 1989, pp. 8.8-8.10.
Xu, et al., J. Biol. Chem.,1994, vol. 269, pp. 3469-3474.
Xu, et al., J. Neurosi., 2001, vol. 21, RC118.
U.S. Appl. No. 12/060,555, filed Apr. 1, 2008, Ellis, et al.
Bartsch, et al., Neuron, vol. 15 pp. 1375-1381 (1995).
Belayev, et al., Brain Research, vol. 739 pp. 88-96 (1996).
Bickel, et al., Advanced Drug Delivery Reviews, vol. 46 pp. 247-274 (1996).
Birch and Lenox, Monoclonal Antibodies: Principles and Applications, John Wilet and Sons Inc. pp. 299-335 (1995).
Chen, et al., Nature vol. 403 (6768) pp. 434-439 (2000).
Coloma, et al., Pharma Research, vol. 17(3) pp. 266-276 (2000).
Depascalis, et al., J. Immunology, vol. 169 pp. 3076-3084 (2002).
Genbank Z18328, accessed Aug. 18, 2008.
Grandpre, et al., Nature, vol. 403(6768) pp. 439-444 (2000).
Jakeman, et al., Exp. Neurol., vol. 154(1) pp. 170-184 (1998).
Kastrup, et al., Journal of the Neurological Sciences, vol. 166 pp. 91-99 (1999).
Kawamata, et al., Proc. Natl. Acad. Sci. USA, vol. 94(15) pp. 8179-8184, 1997.
Lamminmaki, et al., J. Bio. Chem., vol. 276(39) pp. 36687-36694 (2001).
Li, et al., J. of Neurosci. Research, vol. 46(4) pp. 404-414 (1996).
Li, et al., J. of Neurosci. Research, vol. 51(2) pp. 210-217 (1998).
Li, et al., Nature, vol. 369(6483) pp. 747-750 (1994).
Lopate, et al., J. Neurol. Sci., vol. 188(1-2) pp. 67-72 (2001).
Lunn, et al., Brain, vol. 125 pp. 904-911 (2002).
Matsuo, et al., Stroke, vol. 32 pp. 2143-2148 (2001).
McKerracher, et al., Neuron, vol. 13 pp. 805-811 (1994).
Montag, et al, Neuron, vol. 13 pp. 229-246 (1994).
Mukhopadhyay, et al., Neuron. vol. 13 pp. 757-767 (1994).
Prinjha, et al., Nature, vol. 403(6768) pp. 383-384 (2000).
Ribotta, et al., J. Neurosci., vol. 20(13) pp. 5144-5152 (2000).
Sato, et al., Biochem. Biophys. Res. Comm., vol. 163(3) pp. 1473-1480 (1989).
Schafer, et al., Neuron, vol. 16(6) pp. 1107-1113 (1996).
Somogyvari-Vigh, et al., Regulatory Peptides, vol. 91 pp. 89-95 (2000).
Yin, et al., J. Neurosci., vol. 18(6) pp. 1953-1962 (1998).
Bard, et al., Nature Med. 2000; 6(8):916-919.
Benincosa, et al., Pharmacol. Exp. Therapeut. 2000; 292(2):810-816.
Riechman, et al., Reshaping Human Antibodies for Therapy; Nature, vol. 332, Mar. 1988, pp. 323-327.
Whisnant; Stroke 1984; 15(1):160-168.

* cited by examiner

Figure 4

Seq ID No: 18
MGWSCIILFLVATATGVHSQVQLVQSGSELKKPGASVKVSCKASGYTFTNYGMNWVRQAPGQGLEW
MGWINTYTGEPTYADDFTGRFVFSLDTSVSTAYLQISSLKAEDTAVYYCARNPINYYGINYEGYVMDY
WGQGTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPELAGAPSVF
LFPPKPKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEALHNHYTQKSLSLS
PGK

Seq ID No: 19

MGWSCIILFLVATATGVHSDIVMTQSPDSLAVSLGERATINCKSSHSVLYSSNQKNYLAWYQQKPGQP
PKLLIYWASTRESGVPDRFSGSGSGTDFTLTISSLQAEDVAVYYCHQYLSSLTFGQGTKLEIKRTVAAP
SVFIFPPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC

Seq ID No: 20

MGWSCIILFLVATATGVHSQVQLVQSGSELKKPGASVKVSCKASGYTFTNYGMNWVRQAPGQGLEW
MGWINTYTGEPTYADDFTGRFVFSLDTSVSTAYLQISSLKAEDTAVYYCARNPINYYGINYEGYVMDY
WGQGTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEALHNHYTQKSLSLS
PGK

Purified antibody material at concentrations determined by OD280

Figure 8

*Competition ELISA for binding to rat MAG-Fc fusion protein of two purified humanised antibodies and the non-humanised mouse monoclonal antibody*

SEQUENCE LISTING

<160> NUMBER OF SEQ ID NOS: 20

<210> SEQ ID NO 1
<211> LENGTH: 17
<212> TYPE: PRT
<213> ORGANISM: MUS MUSCULUS

<400> SEQUENCE: 1

Lys Ser Ser His Ser Val Leu Tyr Ser Ser Asn Gln Lys Asn Tyr Leu
 1               5                  10                  15
Ala

<210> SEQ ID NO 2
<211> LENGTH: 7
<212> TYPE: PRT
<213> ORGANISM: MUS MUSCULUS

<400> SEQUENCE: 2

Trp Ala Ser Thr Arg Glu Ser
 1               5

<210> SEQ ID NO 3
<211> LENGTH: 8
<212> TYPE: PRT
<213> ORGANISM: MUS MUSCULUS

<400> SEQUENCE: 3

His Gln Tyr Leu Ser Ser Leu Thr
 1               5

<210> SEQ ID NO 4
<211> LENGTH: 5
<212> TYPE: PRT
<213> ORGANISM: MUS MUSCULUS

<400> SEQUENCE: 4

Asn Tyr Gly Met Asn
 1               5

<210> SEQ ID NO 5
<211> LENGTH: 17
<212> TYPE: PRT
<213> ORGANISM: MUS MUSCULUS

<400> SEQUENCE: 5

Trp Ile Asn Thr Tyr Thr Gly Glu Pro Thr Tyr Ala Asp Asp Phe Thr
 1               5                  10                  15
Gly

<210> SEQ ID NO 6
<211> LENGTH: 17
<212> TYPE: PRT
<213> ORGANISM: MUS MUSCULUS

<400> SEQUENCE: 6

Asn Pro Ile Asn Tyr Tyr Gly Ile Asn Tyr Glu Gly Tyr Val Met Asp
 1               5                  10                  15
Tyr

<210> SEQ ID NO 7
<211> LENGTH: 475
<212> TYPE: PRT

<213> ORGANISM: MUS MUSCULUS

<400> SEQUENCE: 7

```
Met Gly Trp Ser Cys Ile Ile Leu Phe Leu Val Ala Thr Ala Thr Gly
 1               5                  10                  15
Val His Ser Glu Ile Gln Leu Val Gln Ser Gly Pro Glu Leu Lys Lys
             20                  25                  30
Pro Gly Glu Thr Asn Lys Ile Ser Cys Lys Ala Ser Gly Tyr Thr Phe
         35                  40                  45
Thr Asn Tyr Gly Met Asn Trp Val Lys Gln Ala Pro Gly Lys Gly Leu
     50                  55                  60
Lys Trp Met Gly Trp Ile Asn Thr Tyr Thr Gly Glu Pro Thr Tyr Ala
 65                  70                  75                  80
Asp Asp Phe Thr Gly Arg Phe Ala Phe Ser Leu Glu Thr Ser Ala Ser
                 85                  90                  95
Thr Ala Tyr Leu Gln Ile Ser Asn Leu Lys Asn Glu Asp Thr Ala Thr
            100                 105                 110
Tyr Phe Cys Ala Arg Asn Pro Ile Asn Tyr Tyr Gly Ile Asn Tyr Glu
        115                 120                 125
Gly Tyr Val Met Asp Tyr Trp Gly Gln Gly Thr Leu Val Thr Val Ser
    130                 135                 140
Ser Ala Ser Thr Lys Gly Pro Ser Val Phe Pro Leu Ala Pro Ser Ser
145                 150                 155                 160
Lys Ser Thr Ser Gly Gly Thr Ala Ala Leu Gly Cys Leu Val Lys Asp
                165                 170                 175
Tyr Phe Pro Glu Pro Val Thr Val Ser Trp Asn Ser Gly Ala Leu Thr
            180                 185                 190
Ser Gly Val His Thr Phe Pro Ala Val Leu Gln Ser Ser Gly Leu Tyr
        195                 200                 205
Ser Leu Ser Ser Val Val Thr Val Pro Ser Ser Ser Leu Gly Thr Gln
    210                 215                 220
Thr Tyr Ile Cys Asn Val Asn His Lys Pro Ser Asn Thr Lys Val Asp
225                 230                 235                 240
Lys Lys Val Glu Pro Lys Ser Cys Asp Lys Thr His Thr Cys Pro Pro
                245                 250                 255
Cys Pro Ala Pro Glu Leu Ala Gly Ala Pro Ser Val Phe Leu Phe Pro
            260                 265                 270
Pro Lys Pro Lys Asp Thr Leu Met Ile Ser Arg Thr Pro Glu Val Thr
        275                 280                 285
Cys Val Val Val Asp Val Ser His Glu Asp Pro Glu Val Lys Phe Asn
    290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                325                 330                 335
Leu His Gln Asp Trp Leu Asn Gly Lys Glu Tyr Lys Cys Lys Val Ser
            340                 345                 350
Asn Lys Ala Leu Pro Ala Pro Ile Glu Lys Thr Ile Ser Lys Ala Lys
        355                 360                 365
Gly Gln Pro Arg Glu Pro Gln Val Tyr Thr Leu Pro Pro Ser Arg Asp
    370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
```

```
                   405                 410                 415
Asn Asn Tyr Lys Thr Thr Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys
465                 470                 475

<210> SEQ ID NO 8
<211> LENGTH: 238
<212> TYPE: PRT
<213> ORGANISM: Artificial Sequence
<220> FEATURE:
<223> OTHER INFORMATION: Light chain

<400> SEQUENCE: 8

Met Gly Trp Ser Cys Ile Ile Leu Phe Leu Val Ala Thr Ala Thr Gly
1               5                   10                  15

Val His Ser Asn Ile Met Met Thr Gln Ser Pro Ser Ser Leu Ala Val
            20                  25                  30

Ser Ala Gly Glu Lys Val Thr Met Ser Cys Lys Ser Ser His Ser Val
        35                  40                  45

Leu Tyr Ser Ser Asn Gln Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ile Asn Val His Thr Glu Asp Leu Ala Val Tyr Tyr
            100                 105                 110

Cys His Gln Tyr Leu Ser Ser Leu Thr Phe Gly Thr Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 9
<211> LENGTH: 475
<212> TYPE: PRT
<213> ORGANISM: Artificial Sequence
<220> FEATURE:
<223> OTHER INFORMATION: Heavy chain

<400> SEQUENCE: 9

Met Gly Trp Ser Cys Ile Ile Leu Phe Leu Val Ala Thr Ala Thr Gly
```

-continued

```
                1               5                  10                 15
          Val His Ser Glu Ile Gln Leu Val Gln Ser Gly Pro Glu Leu Lys Lys
                         20                  25                  30

Pro Gly Glu Thr Asn Lys Ile Ser Cys Lys Ala Ser Gly Tyr Thr Phe
                         35                  40                  45

Thr Asn Tyr Gly Met Asn Trp Val Lys Gln Ala Pro Gly Lys Gly Leu
                50                  55                  60

Lys Trp Met Gly Trp Ile Asn Thr Tyr Thr Gly Glu Pro Thr Tyr Ala
          65                  70                  75                  80

Asp Asp Phe Thr Gly Arg Phe Ala Phe Ser Leu Glu Thr Ser Ala Ser
                              85                  90                  95

Thr Ala Tyr Leu Gln Ile Ser Asn Leu Lys Asn Glu Asp Thr Ala Thr
                              100                 105                 110

Tyr Phe Cys Ala Arg Asn Pro Ile Asn Tyr Tyr Gly Ile Asn Tyr Glu
                         115                 120                 125

Gly Tyr Val Met Asp Tyr Trp Gly Gln Gly Thr Leu Val Thr Val Ser
                    130                 135                 140

Ser Ala Ser Thr Lys Gly Pro Ser Val Phe Pro Leu Ala Pro Ser Ser
          145                 150                 155                 160

Lys Ser Thr Ser Gly Gly Thr Ala Ala Leu Gly Cys Leu Val Lys Asp
                              165                 170                 175

Tyr Phe Pro Glu Pro Val Thr Val Ser Trp Asn Ser Gly Ala Leu Thr
                         180                 185                 190

Ser Gly Val His Thr Phe Pro Ala Val Leu Gln Ser Ser Gly Leu Tyr
                    195                 200                 205

Ser Leu Ser Ser Val Val Thr Val Pro Ser Ser Ser Leu Gly Thr Gln
                    210                 215                 220

Thr Tyr Ile Cys Asn Val Asn His Lys Pro Ser Asn Thr Lys Val Asp
          225                 230                 235                 240

Lys Lys Val Glu Pro Lys Ser Cys Asp Lys Thr His Thr Cys Pro Pro
                         245                 250                 255

Cys Pro Ala Pro Glu Leu Leu Gly Gly Pro Ser Val Phe Leu Phe Pro
                    260                 265                 270

Pro Lys Pro Lys Asp Thr Leu Met Ile Ser Arg Thr Pro Glu Val Thr
               275                 280                 285

Cys Val Val Val Asp Val Ser His Glu Asp Pro Glu Val Lys Phe Asn
                    290                 295                 300

Trp Tyr Val Asp Gly Val Glu Val His Asn Ala Lys Thr Lys Pro Arg
          305                 310                 315                 320

Glu Glu Gln Tyr Asn Ser Thr Tyr Arg Val Val Ser Val Leu Thr Val
                              325                 330                 335

Leu His Gln Asp Trp Leu Asn Gly Lys Glu Tyr Lys Cys Lys Val Ser
                         340                 345                 350

Asn Lys Ala Leu Pro Ala Pro Ile Glu Lys Thr Ile Ser Lys Ala Lys
                    355                 360                 365

Gly Gln Pro Arg Glu Pro Gln Val Tyr Thr Leu Pro Pro Ser Arg Asp
               370                 375                 380

Glu Leu Thr Lys Asn Gln Val Ser Leu Thr Cys Leu Val Lys Gly Phe
          385                 390                 395                 400

Tyr Pro Ser Asp Ile Ala Val Glu Trp Glu Ser Asn Gly Gln Pro Glu
                              405                 410                 415

Asn Asn Tyr Lys Thr Thr Pro Val Leu Asp Ser Asp Gly Ser Phe
                         420                 425                 430
```

```
Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys
465                 470                 475

<210> SEQ ID NO 10
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 10

Gln Val Gln Leu Val Gln Ser Gly Ser Glu Leu Lys Lys Pro Gly Ala
  1               5                  10                  15

Ser Val Lys Val Ser Cys Lys Ala Ser Gly Tyr Thr Phe Thr Asn Tyr
             20                  25                  30

Gly Met Asn Trp Val Arg Gln Ala Pro Gly Gln Gly Leu Glu Trp Met
         35                  40                  45

Gly Trp Ile Asn Thr Tyr Thr Gly Glu Pro Thr Tyr Ala Asp Asp Phe
     50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Asn Pro Ile Asn Tyr Tyr Gly Ile Asn Tyr Glu Gly Tyr Val
                100                 105                 110

Met Asp Tyr Trp Gly Gln Gly Thr Leu Val Thr Val Ser Ser
            115                 120                 125

<210> SEQ ID NO 11
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 11

Gln Val Gln Leu Val Gln Ser Gly Ser Glu Leu Lys Lys Pro Gly Ala
  1               5                  10                  15

Ser Val Lys Val Ser Cys Lys Ala Ser Gly Tyr Thr Phe Thr Asn Tyr
             20                  25                  30

Gly Met Asn Trp Val Arg Gln Ala Pro Gly Gln Gly Leu Glu Trp Met
         35                  40                  45

Gly Trp Ile Asn Thr Tyr Thr Gly Glu Pro Thr Tyr Ala Asp Asp Phe
     50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Asn Pro Ile Asn Tyr Tyr Gly Ile Asn Tyr Glu Gly Tyr Val
                100                 105                 110

Met Asp Tyr Trp Gly Gln Gly Thr Leu Val Thr Val Ser Ser
            115                 120                 125

<210> SEQ ID NO 12
<211> LENGTH: 126
```

```
<212> TYPE: PRT
<213> ORGANISM: Artificial Sequence
<220> FEATURE:
<223> OTHER INFORMATION: Heavy chain variable region

<400> SEQUENCE: 12

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Thr Tyr Phe Cys
                85                  90                  95

Ala Arg Asn Pro Ile Asn Tyr Tyr Gly Ile Asn Tyr Glu Gly Tyr Val
            100                 105                 110

Met Asp Tyr Trp Gly Gln Gly Thr Leu Val Thr Val Ser Ser
        115                 120                 125

<210> SEQ ID NO 13
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 13

Gln Val Gln Leu Val Gln Ser Gly Ser Glu Leu Lys Lys Pro Gly Ala
 1               5                  10                  15

Ser Asn Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Thr Tyr Phe Cys
                85                  90                  95

Ala Arg Asn Pro Ile Asn Tyr Tyr Gly Ile Asn Tyr Glu Gly Tyr Val
            100                 105                 110

Met Asp Tyr Trp Gly Gln Gly Thr Leu Val Thr Val Ser Ser
        115                 120                 125

<210> SEQ ID NO 14
<211> LENGTH: 115
<212> TYPE: PRT
<213> ORGANISM: Artificial Sequence
<220> FEATURE:
<223> OTHER INFORMATION: Light chain variable region

<400> SEQUENCE: 14

Asp Ile Val Met Thr Gln Ser Pro Asp Ser Leu Ala Val Ser Leu Gly
 1               5                  10                  15

Glu Arg Ala Thr Ile Asn Cys Lys Ser Ser His Ser Val Leu Tyr Ser
            20                  25                  30
```

```
Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys His Gln
                85                  90                  95

Tyr Leu Ser Ser Leu Thr Phe Gly Gln Gly Thr Lys Leu Glu Ile Lys
                100                 105                 110

Arg Thr Val
        115

<210> SEQ ID NO 15
<211> LENGTH: 115
<212> TYPE: PRT
<213> ORGANISM: Artificial Sequence
<220> FEATURE:
<223> OTHER INFORMATION: Light chain variable region

<400> SEQUENCE: 15

Asp Ile Val Met Thr Gln Ser Pro Asp Ser Leu Ala Val Ser Leu Gly
 1               5                  10                  15

Glu Arg Ala Thr Ile Asn Cys Lys Ser Ser His Ser Val Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ile Asn Leu Gln Ala Glu Asp Val Ala Val Tyr Tyr Cys His Gln
                85                  90                  95

Tyr Leu Ser Ser Leu Thr Phe Gly Gln Gly Thr Lys Leu Glu Ile Lys
                100                 105                 110

Arg Thr Val
        115

<210> SEQ ID NO 16
<211> LENGTH: 115
<212> TYPE: PRT
<213> ORGANISM: Artificial Sequence
<220> FEATURE:
<223> OTHER INFORMATION: Light chain variable region

<400> SEQUENCE: 16

Asp Ile Val Met Thr Gln Ser Pro Asp Ser Leu Ala Val Ser Leu Gly
 1               5                  10                  15

Glu Arg Ala Thr Ile Asn Cys Lys Ser Ser His Ser Val Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu His Thr Glu Asp Val Ala Val Tyr Tyr Cys His Gln
                85                  90                  95
```

```
Tyr Leu Ser Ser Leu Thr Phe Gly Gln Gly Thr Lys Leu Glu Ile Lys
            100                 105                 110

Arg Thr Val
        115

<210> SEQ ID NO 17
<211> LENGTH: 115
<212> TYPE: PRT
<213> ORGANISM: Artificial Sequence
<220> FEATURE:
<223> OTHER INFORMATION: Light chain variable region

<400> SEQUENCE: 17

Asp Ile Val Met Thr Gln Ser Pro Asp Ser Leu Ala Val Ser Leu Gly
 1               5                  10                  15

Glu Arg Ala Thr Ile Asn Cys Lys Ser Ser His Ser Val Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ile Asn Leu His Thr Glu Asp Val Ala Val Tyr Tyr Cys His Gln
                85                  90                  95

Tyr Leu Ser Ser Leu Thr Phe Gly Gln Gly Thr Lys Leu Glu Ile Lys
            100                 105                 110

Arg Thr Val
        115

<210> SEQ ID NO 18
<211> LENGTH: 475
<212> TYPE: PRT
<213> ORGANISM: Artificial Sequence
<220> FEATURE:
<223> OTHER INFORMATION: Heavy chain

<400> SEQUENCE: 18

Met Gly Trp Ser Cys Ile Ile Leu Phe Leu Val Ala Thr Ala Thr Gly
 1               5                  10                  15

Val His Ser Gln Val Gln Leu Val Gln Ser Gly Ser Glu Leu Lys Lys
                20                  25                  30

Pro Gly Ala Ser Val Lys Val Ser Cys Lys Ala Ser Gly Tyr Thr Phe
            35                  40                  45

Thr Asn Tyr Gly Met Asn Trp Val Arg Gln Ala Pro Gly Gln Gly Leu
        50                  55                  60

Glu Trp Met Gly Trp Ile Asn Thr Tyr Thr Gly Glu Pro Thr Tyr Ala
65                  70                  75                  80

Asp Asp Phe Thr Gly Arg Phe Val Phe Ser Leu Asp Thr Ser Val Ser
                85                  90                  95

Thr Ala Tyr Leu Gln Ile Ser Ser Leu Lys Ala Glu Asp Thr Ala Val
            100                 105                 110

Tyr Tyr Cys Ala Arg Asn Pro Ile Asn Tyr Tyr Gly Ile Asn Tyr Glu
        115                 120                 125

Gly Tyr Val Met Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160
```

Lys Ser Thr Ser Gly Gly Thr Ala Ala Leu Gly Cys Leu Val Lys Asp
            165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Leu Gly Thr Gln
            210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
            245                 250                 255

Cys Pro Ala Pro Glu Leu Ala Gly Ala Pro Ser Val Phe Leu Phe Pro
            260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
            325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
            370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys
465                 470                 475

<210> SEQ ID NO 19
<211> LENGTH: 238
<212> TYPE: PRT
<213> ORGANISM: Artificial Sequence
<220> FEATURE:
<223> OTHER INFORMATION: Light chain

<400> SEQUENCE: 19

Met Gly Trp Ser Cys Ile Ile Leu Phe Leu Val Ala Thr Ala Thr Gly
1               5                   10                  15

Val His Ser Asp Ile Val Met Thr Gln Ser Pro Asp Ser Leu Ala Val
            20                  25                  30

Ser Leu Gly Glu Arg Ala Thr Ile Asn Cys Lys Ser Ser His Ser Val
            35                  40                  45

```
Leu Tyr Ser Ser Asn Gln Lys Asn Tyr Leu Ala Trp Tyr Gln Gln Lys
         50                  55                  60

Pro Gly Gln Pro Pro Lys Leu Leu Ile Tyr Trp Ala Ser Thr Arg Glu
 65                  70                  75                  80

Ser Gly Val Pro Asp Arg Phe Ser Gly Ser Gly Ser Gly Thr Asp Phe
                 85                  90                  95

Thr Leu Thr Ile Ser Ser Leu Gln Ala Glu Asp Val Ala Val Tyr Tyr
            100                 105                 110

Cys His Gln Tyr Leu Ser Ser Leu Thr Phe Gly Gln Gly Thr Lys Leu
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 20
<211> LENGTH: 475
<212> TYPE: PRT
<213> ORGANISM: Artificial Sequence
<220> FEATURE:
<223> OTHER INFORMATION: Heavy chain

<400> SEQUENCE: 20

Met Gly Trp Ser Cys Ile Ile Leu Phe Leu Val Ala Thr Ala Thr Gly
 1               5                  10                  15

Val His Ser Gln Val Gln Leu Val Gln Ser Gly Ser Glu Leu Lys Lys
                20                  25                  30

Pro Gly Ala Ser Val Lys Val Ser Cys Lys Ala Ser Gly Tyr Thr Phe
             35                  40                  45

Thr Asn Tyr Gly Met Asn Trp Val Arg Gln Ala Pro Gly Gln Gly Leu
 50                  55                  60

Glu Trp Met Gly Trp Ile Asn Thr Tyr Thr Gly Glu Pro Thr Tyr Ala
 65                  70                  75                  80

Asp Asp Phe Thr Gly Arg Phe Val Phe Ser Leu Asp Thr Ser Val Ser
                 85                  90                  95

Thr Ala Tyr Leu Gln Ile Ser Ser Leu Lys Ala Glu Asp Thr Ala Val
            100                 105                 110

Tyr Tyr Cys Ala Arg Asn Pro Ile Asn Tyr Tyr Gly Ile Asn Tyr Glu
            115                 120                 125

Gly Tyr Val Met Asp Tyr Trp Gly Gln Gly Thr Leu Val Thr Val Ser
            130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
```

```
                          180                 185                 190
Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
            210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
            245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
            290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
            325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
            370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys
465                 470                 475
```

THERAPEUTICAL USE OF ANTI-MYELIN ASSOCIATED GLYCOPROTEIN (MAG) ANTIBODIES

CROSS-REFERENCE TO RELATED APPLICATIONS

This application is filed pursuant to 35 USC 371 as a United States National Phase Application of International Patent Application Serial No. PCT/EP2004/001016 filed on Feb. 2, 2004, which claims priority from 0306309.6 filed on Mar. 19, 2003 in the United Kingdom.

FIELD OF THE INVENTION

The present invention relates to a method of treatment of neurological diseases. In particular the invention relates to the use of anti-MAG antibodies to promote oligodendrocyte survival in a human, particularly following an oxidative stress event.

BACKGROUND OF THE INVENTION

Myelin-associated glycoprotein is a cell surface transmembrane molecule expressed on the surface of myelin consisting of five extracellular immunoglobulin domains, a single transmembrane domain and an intracellular domain. MAG expression is restricted to myelinating glia: oligodendrocytes in the central nervous system and Scwann cells in the peripheral nervous system. MAG interacts with neuronal receptor(s) which initiates bi-directional signalling between neurons and glia. The effect of MAG binding to neuronal receptors is known to result in inhibition of neurite outgrowth in vitro. Based on this in vitro data, antagonists of MAG have been postulated as useful for the promotion of axonal sprouting following injury (WO9522344, WO9701352 and WO9707810), although these claims are not supported by in vivo data. WO02/062383 discloses that an anti-MAG antibody, when administered directly into the brain or intravenously following focal cerebral ischaemia in the rat (a model of stroke) provides neuroprotection and enhances functional recovery.

Evidence in the literature suggests that MAG also mediates signalling intoglial cells, but the functional significance of this has not been understood. It has been reported that engagement of MAG expressed at the surface of a CHO cell using an antibody leads to the activation of fyn kinase (Umemori et al 1994, Nature, 367, 572-576). Furthermore, MAG knockout animals exhibit defects in myelin which resemble aspects of the defective changes observed in the brains of multiple sclerosis and encephalomyelitis patients (Lassman et al., Glia, 19, 104-110).

It has now been found that an anti-MAG monoclonal antibody previously shown to provide benefit in a rat model of stroke protects oligodendrocytes from oxidative-induced cell death in vitro. Furthermore, an increased number of histologically intact oligodendroctyes were observed in the brains of rats treated with anti-MAG compared to control antibody following middle-cerebral artery occlusion. Therefore anti-MAG antibodies (or MAG antagonists) may provide dual activities of promotion of neuronal regeneration as well as surprisingly triggering pathways which promote oligodendrocyte survival.

Oligodendrocyte damage or degeneration is observed in several neurological diseases including Alzheimer's disease (e.g. Roher et al, 2002, Biochemistry 41:11080-90; Xu et al, 2001, J. Neurosci. 2001 21:RC118), spinal cord injury (e.g. Crowe et al, 1997, Nature Medicine, 1997, 3:73-6; Beattie et al, 2002, Neuron 36:375-86), traumatic brain injury (e.g. Castejon et al, 2000, Brain Inj. 2000 April; 14(4):303-17) and multiple sclerosis. Therefore anti-MAG antibody or antagonists could provide benefit in these diseases in addition to stroke by both promoting neuronal regeneration and preventing oligodendrocyte cell death.

BRIEF SUMMARY OF THE INVENTION

In one aspect, the present invention provides a method of promoting oligodendrocyte survival in a human suffering or at risk of developing a neurological disease which comprises administering to said human a therapeutically effective amount of an anti-MAG antibody, including altered antibodies or a functional fragment thereof.

In another aspect, the invention provides the use of an anti-MAG antibody, including altered antibodies or a functional fragment thereof in the preparation of a medicament for the promotion of oligodendrocyte survival in a human suffering or at risk of developing a neurological disease.

Other aspects and advantages of the present invention are described further in the detailed description and the preferred embodiments thereof.

DESCRIPTION OF THE FIGURES

FIG. 4: Humanised anti-MAG sequences

FIG. 8: Competition ELISA with mouse and humanised anti-MAG antibodies

DETAILED DESCRIPTION ON THE INVENTION

Figure 1:
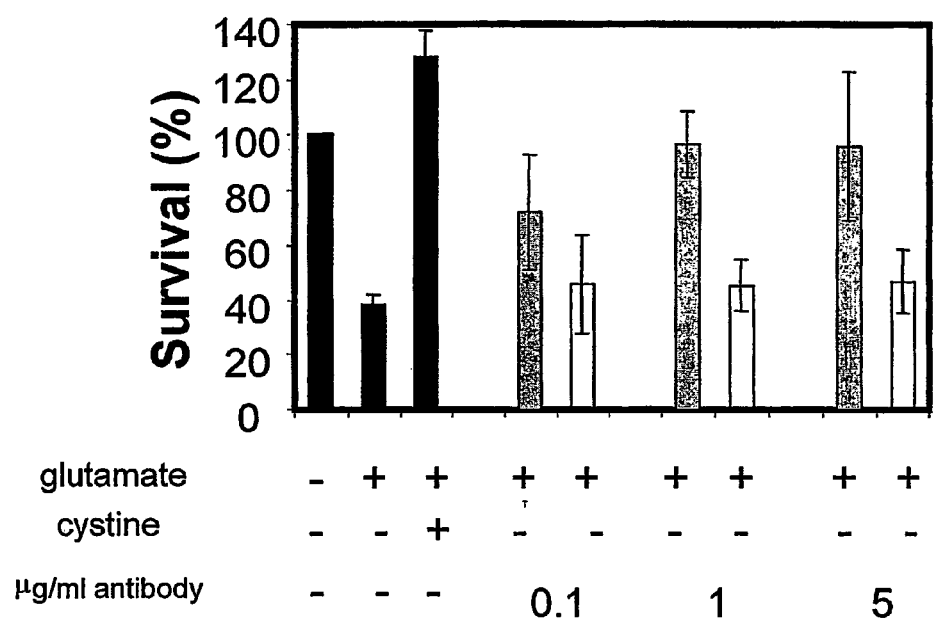
FIG. 1: Anti-MAG monoclonal antibody protects oligodendrocytes from glutamate mediated cell death.

Neurological diseases which may be treated by the method of the present invention include stroke, traumatic brain injury and spinal cord injury as well as chronic diseases including Alzheimer's disease, fronto-temporal dementias (tauopathies), peripheral neuropathy, Parkinson's disease, Huntington's disease and multiple sclerosis. Anti-MAG mabs therefore may be useful in the treatment of these diseases as well as any other disorders related to oxidative stress and/or the degeneration of myelin or oligodendrocytes.

It has now been found that an anti-MAG monoclonal antibody, described (Poltorak et al (1987) *Journal of Cell Biology* 105, 1893-1899, DeBellard et al (1996) *Mol. Cell. Neurosci.* 7, 89-101; Tang et al (1997) *Mol. Cell. Neurosci.* 9, 333-346; Torigoe K and Lundborg G (1997) *Exp. Neurology* 150, 254-262) and commercially available (MAB1567 (Chemicon)) when administered either directly into the brain or intravenously following focal cerebral ischaemia in the rat (a model of stroke) directly protects oligodendrocytes from oxidative induced cell death. This antibody is a murine antibody. Although murine antibodies are often used as diagnostic agents their utility as a therapeutic has been proven in only a few cases. Their limited application is in part due to the repeated administration of murine monoclonals to humans usually elicits human immune responses against these molecules. To overcome these intrinsic undesirable properties of murine monoclonals "altered" antibodies designed to incorporate regions of human antibodies have been developed and are well established in the art. For example, a humanised antibody contains complementarity determining regions ("CDR's") of non human origin and the majority of the rest of the structure is derived from a human antibody.

The antibody useful in the invention is preferably a fully human antibody or an altered antibody, preferably a monoclonal antibody (mAb) and is more preferably chimeric, humanised or reshaped, more preferably humanised.

The human or altered antibody preferably has the structure of a natural antibody or fragment thereof. The antibody may therefore comprise a complete antibody, a $(Fab^1)_2$ fragment, a Fab fragment, a light chain dimer or a heavy chain dimer. The antibody may be an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain.

Preferably the antibody or functional fragment thereof useful in the present invention binds to MAG and comprises one or more of the following CDR's. The CDR's are identified as described by Kabat (Kabat et al. (1991) Sequences of proteins of immunological interest; Fifth Edition; US Department of Health and Human Services; NIH publication No 91-3242. CDRs preferably are as defined by Kabat but following the principles of protein structure and folding as defined by Chothia and Lesk, (Chothia et al., (1989) Conformations of immunoglobulin hypervariable regions; Nature 342, p 877-883) it will be appreciated that additional residues may also be considered to be part of the antigen binding region and are thus encompassed by the present invention.

| Light chain CDRs | | |
|---|---|---|
| CDR | According to Kabat | |
| L1 | KSSHSVLYSSNQKNYLA | (Seq ID No 1) |
| L2 | WASTRES | (Seq ID No 2) |
| L3 | HQYLSSLT | Seq ID No 3) |

| Heavy chain CDRs | | |
|---|---|---|
| CDR | According to Kabat | |
| H1 | NYGMN | (Seq ID No 4) |
| H2 | WINTYTGEPTYADDFTG | (Seq ID No 5) |
| H3 | NPINYYGINYEGYVMDY | (Seq ID No 6) |

The present invention also relates to the use of an antibody which binds to the same epitope as an antibody having the CDRs described above. Competitive inhibition assays are used for mapping of the epitopes on an antigen. Thus there is also provided the use of an anti-MAG antibody (altered or unaltered) which competitvely inhibits the binding of the altered antibody having the CDRs described supra to MAG, preferably human MAG.

More preferably, the altered antibody or functional fragment thereof useful in the present invention comprises a heavy chain variable domain which comprises one or more CDR's selected from CDRH1, CDRH2 and CDRH3 and for a light chain variable domain which comprises one or more CDRs selected from CDRL1, CDRL2 and CDRL3.

Most preferably the altered anti-Mag antibody or functional fragment thereof useful in the present invention comprises:
a) a heavy chain variable domain ($V_H$) which comprises in sequence CDRH1, CDRH2 and CDRH3,
and/or
b) a light chain variable domain ($V_L$) which comprises in sequence CDRL1, CDRL2 and CDRL3

As discussed above, altered antibodies include chimeric antibodies which comprise variable regions deriving from one species linked to constant regions from other species. Chimeric mouse-human anti-MAG immunoglobulin light and heavy chains useful in the present invention are provided below:

Sequence of a mouse/human chimeric anti-MAG antibody heavy chain in which the murine anti-MAG heavy chain variable region is associated with a functional immunoglobulin secretion signal sequence, and with an altered form of the human IgG1 constant region, in which Kabat residues 248 and 250 have been mutated to alanine in order to disable the effector functions of binding to FcγRI and complement protein C1q (Duncan, A. R. and Winter, G. Localization of the C1q binding site on antibodies by surface scanning. Nature 332, 738-740, 1988. Duncan, A. R., Woolf, J. M., Partridge, L. J., Burton, D. R. and Winter, G.

(Seq ID No 7)
MGWSCIILFLVATATGVHSEIQLVQSGPELKKPGETNKISCKASGYTFTN

YGMNWVKQAPGKGLKWMGWINTYTGEPTYADDFTGRFAFSLETSASTAYL

QISNLKNEDTATYFCARNPINYYGINYEGYVMDYWGQGTLVTVSSASTKG

PSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDK

THTCPPCPAPELAGAPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNV

FSCSVMHEALHNHYTQKSLSLSPGK

Sequence of a mouse/human chimeric anti-MAG antibody light chain in which the murine anti-MAG light chain variable region is associated with a functional immunoglobulin secretion signal sequence, and with the human kappa constant region.

(Seq ID No 8)
MGWSCIILFLVATATGVHSNIMMTQSPSSLAVSAGEKVTMSCKSSHSVLY

SSNQKNYLAWYQQKPGQSPKLLIYWASTRESGVPDRFTGSGSGTDFTLTI

INVHTEDLAVYYCHQYLSSLTFGTGTKLEIKRTVAAPSVFIFPPSDEQLK

SGTASVVCLLNNFYPREAKVQWKVDNALQSGNSQESVTEQDSKDSTYSLS

STLTLSKADYEKHKVYACEVTHQGLSSPVTKSFNRGEC

Sequence of a mouse/human chimeric anti-MAG antibody heavy chain which provides the amino acid sequence of a chimeric immunoglobulin heavy chain in which the murine anti-MAG heavy chain variable region is associated with a functional immunoglobulin secretion signal sequence, and with a wild-type type form of the human IgG1 constant region.

(Seq ID No 9)
MGWSCIILFLVATATGVHSEIQLVQSGPELKKPGETNKISCKASGYTFTN

YGMNWVKQAPGKGLKWMGWINTYTGEPTYADDFTGRFAFSLETSASTAYL

QISNLKNEDTATYFCARNPINYYGINYEGYVMDYWGQGTLVTVSSASTKG

PSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDK

THTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNV

FSCSVMHEALHNHYTQKSLSLSPGK

Thus for example the present invention includes the use of an altered antibody comprising a heavy chain Sequence ID No 9 or 7 and/or a light chain Seq ID No 8.

Mouse-human chimeras using human 1gG1, 1gG2, 1gG3, 1gG4, 1GA, 1gE, 1gM, 1gD constant regions may be produced, as may chimeras associating the mouse variable regions with heavy or light chain constant regions from non-human species.

Most preferably, the antibody for use in the present invention is humanised antibody or functional fragment thereof that binds to one of MAG and comprises a heavy chain variable region comprising the following amino acid sequences:

QVQLVQSGSELKKPGASVKVSCKASGYTFTNYGMNW   (Seq ID No 10)
VRQAPGQGLEWMGWINTYTGEPTYADDFTGRFVFSL
DTSVSTAYLQISSLKAEDTAVYYCARNPINYYGINY
EGYVMDYWGQGTLVTVSS

QVQLVQSGSELKKPGASVKVSCKASGYTFTNYGMNW   (Seq ID No 11)
VRQAPGQGLEWMGWINTYTGEPTYADDFTGRFVFSL
DTSVSTAYLQISSLKAEDTAVYFCARNPINYYGINY
EGYVMDYWGQGTLVTVSS

QVQLVQSGSELKKPGASVKVSCKASGYTFTNYGMNW   (Seq ID No 12)
VRQAPGQGLEWMGWINTYTGEPTYADDFTGRFVFSL
DTSVSTAYLQISSLKAEDTATYFCARNPINYYGINY
EGYVMDYWGQGTLVTVSS

QVQLVQSGSELKKPGASNKVSCKASGYTFTNYGMNW   (Seq ID No 13)
VRQAPGQGLEWMGWINTYTGEPTYADDFTGRFVFSL
DTSVSTAYLQISSLKAEDTATYFCARNPINYYGINY
EGYVMDYWGQGTLVTVSS

In each of these cases each of the 4 heavy chains are preferably combined with one of 4 light chain variable regions:

DIVMTQSPDSLAVSLGERATINCKSSHSVLYSSNQK   (Seq ID No 14)
NYLAWYQQKPGQPPKLLIYWASTRESGVPDRFSGSG
SGTDFTLTISSLQAEDVAVYCHQYLSSLTFGQGTK
LEIKRTV

DIVMTQSPDSLAVSLGERATINCKSSHSVLYSSNQK   (Seq ID No 15)
NYLAWYQQKPGQPPKLLIYWASTRESGVPDRFSGSG
SGTDFTLTIINLQAEDVAVYCHQYLSSLTFGQGTK
LEIKRTV

DIVMTQSPDSLAVSLGERATINCKSSHSVLYSSNQK   (Seq ID No 16)
NYLAWYQQKPGQPPKLLIYWASTRESGVPDRFSGSG
SGTDFTLTISSLHTEDVAVYYCHQYLSSLTFGQGTK
LEIKRTV

DIVMTQSPDSLAVSLGERATINCKSSHSVLYSSNQK   (Seq ID No 17)
NYLAWYQQKPGQPPKLLIYWASTRESGVPDRFSGSG
SGTDFTLTIINLHTEDVAVYYCHQYLSSLTFGQGTK
LEIKRTV

Preferred antibodies for use in the present invention therefore include all combinations of preferred elements listed above. In particular the invention includes all combinations of each of the above 4 heavy chains (Seq ID No 10-13) with each of the 4 light chains (Seq ID No 14-17).

In a particular further aspect of the invention there is provided a humanised antibody or functional fragment thereof which binds to MAG which comprises the heavy chain variable region of Sequence ID No 10, 11 or 12 together with a light chain variable region comprising amino acid Sequences, Sequence ID No 14, 15, 16, or 17:

The constant region is selected according to the functionality required. Normally an IgG1 will demonstrate lytic ability through binding to complement and will mediate ADCC (antibody dependent cell cytotoxicity). An IgG4 will be preferred if an non-cytototoxic blocking antibody is required. However, IgG4 antibodies can demonstrate instability in production and therefore is may be more preferable to modify the generally more stable IgG1. Suggested modifications are described in EP0307434, preferred modifications include at positions 235 and 237. The invention therefore provides a lytic or a non-lytic form of an antibody according to the invention.

In a preferred aspect the altered antibody useful in the present invention is class IgG, more preferably IgG1.

In preferred forms therefore the antibody of the invention is a full length non-lytic IgG1 antibody having the CDRs described supra. In most preferred forms we provide a full length non-lytic IgG1 antibody having the CDRs of SEQ.I.D.NO:10 and 14 and a full length non-lytic IgG1 antibody having the CDRs of SEQ.I.D.NO: 12 and 16.

In a further aspect of the present invention there is provided a humanised antibody comprising:
  a heavy chain variable fragment comprising SEQ ID no 10, 11 or 12
  and a constant part or fragment thereof of a human heavy chain
  and
  a light chain variable fragment comprising SEQ ID No 14, 15, 16, or 17:
  and a constant part or fragment thereof of a human light chain.

In a preferred aspect the humanised antibody is class IgG more preferably IgG1. Preferred antibodies of the invention comprise:
  Heavy chain variable region comprising Seq ID No 10 and light chain variable region comprising Seq ID No 14;
  Heavy chain variable region comprising Seq ID No 10 and light chain variable region comprising Seq ID No 15;
  Heavy chain variable region comprising Seq ID No 10 and light chain variable region comprising Seq ID No 16;
  Heavy chain variable region comprising Seq ID No 10 and light chain variable region comprising Seq ID No 7
  Heavy chain variable region comprising Seq ID No 11 and light chain variable region comprising Seq ID No 14;
  Heavy chain variable region comprising Seq ID No 11 and light chain variable region comprising Seq ID No 15;
  Heavy chain variable region comprising Seq ID No 11 and light chain variable region comprising Seq ID No 16;

Heavy chain variable region comprising Seq ID No 11 and light chain variable region comprising Seq ID No 17.
Heavy chain variable region comprising Seq ID No 12 and light chain variable region comprising Seq ID No 14;
Heavy chain variable region comprising Seq ID No 12 and light chain variable region comprising Seq ID No 15;
Heavy chain variable region comprising Seq ID No 12 and light chain variable region comprising Seq ID No 16;
Heavy chain variable region comprising Seq ID No 12 and light chain variable region comprising Seq ID No 17.

"Neutralising" refers to substantial inhibition of MAG function including its binding to neurones and inhibition of neurite outgrowth.

"Substantial inhibition" refers to 75%, more preferably 85%, most preferably 95% inhibition measured in in vitro tests.

"Altered antibody" refers to a protein encoded by an altered immunoglobulin coding region, which may be obtained by expression in a selected host cell. Such altered antibodies include engineered antibodies (e.g., chimeric, reshaped, humanized or vectored antibodies) or antibody fragments lacking all or part of an immunoglobulin constant region, e.g., Fv, Fab, or F(ab)$_2$ and the like.

"Altered immunoglobulin coding region" refers to a nucleic acid sequence encoding altered antibody. When the altered antibody is a CDR-grafted or humanized antibody, the sequences that encode the complementarity determining regions (CDRs) from a non-human immunoglobulin are inserted into a first immunoglobulin partner comprising human variable framework sequences. Optionally, the first immunoglobulin partner is operatively linked to a second immunoglobulin partner.

"First immunoglobulin partner" refers to a nucleic acid sequence encoding a human framework or human immunoglobulin variable region in which the native (or naturally-occurring) CDR-encoding regions are replaced by the CDR-encoding regions of a donor antibody. The human variable region can be an immunoglobulin heavy chain, a light chain (or both chains), an analog or functional fragments thereof. Such CDR regions, located within the variable region of antibodies (immunoglobulins) can be determined by known methods in the art. For example Kabat et al. (*Sequences of Proteins of Immunological Interest,* 4th Ed., U.S. Department of Health and Human Services, National Institutes of Health (1987)) disclose rules for locating CDRs. In addition, computer programs are known which are useful for identifying CDR regions/structures.

"Second immunoglobulin partner" refers to another nucleotide sequence encoding a protein or peptide to which the first immunoglobulin partner is fused in frame or by means of an optional conventional linker sequence (i.e., operatively linked). Preferably it is an immunoglobulin gene. The second immunoglobulin partner may include a nucleic acid sequence encoding the entire constant region for the same (i.e., homologous—the first and second altered antibodies are derived from the same source) or an additional (i.e., heterologous) antibody of interest. It may be an immunoglobulin heavy chain or light chain (or both chains as part of a single polypeptide). The second immunoglobulin partner is not limited to a particular immunoglobulin class or isotype. In addition, the second immunoglobulin partner may comprise part of an Immunoglobulin constant region, such as found in a Fab, or F(ab)$_2$ (i.e., a discrete part of an appropriate human constant region or framework region). Such second immunoglobulin partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

The terms Fv, Fc, Fd, Fab, or F(ab)$_2$ are used with their standard meanings (see, e.g., Harlow et al., *Antibodies A Laboratory Manual,* Cold Spring Harbor Laboratory, (1988)).

As used herein, an "engineered antibody" describes a type of altered antibody, i.e., a full-length synthetic antibody (e.g., a chimeric, reshaped or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., *Proc. Natl. Acad Sci USA,* 86:10029-10032 (1989), Hodgson et al., *Bio/Technology,* 9:421 (1991)).

"Reshaped human antibody" refers to an altered antibody in which minimally at least one CDR from a first human monoclonal donor antibody is substituted for a CDR in a second human acceptor antibody. Preferably all six CDRs are replaced. More preferably an entire antigen combining region (e.g., Fv, Fab or F(ab')$_2$) from a first human donor monoclonal antibody is substituted for the corresponding region in a second human acceptor monoclonal antibody. Most preferably the Fab region from a first human donor is operatively linked to the appropriate constant regions of a second human acceptor antibody to form a full length monoclonal antibody.

A "vectored antibody" refers to an antibody to which an agent has been attached to improve transport through the blood brain barrier (BBB). The attachment may be chemical or alternatively the moeity can be engineered into the antibody. One example is to make a chimera with an antibody directed towards a brain capilliary endothelial cell receptor e.g. an anti-insulin receptor antibody or anti-transferrin receptor antibody (Saito et al (1995) *Proc. Natl. Acad. Sci. USA* 92 10227-31; Pardridge et al (1995) *Pharm. Res.* 12 807-816; Broadwell et al (1996) *Exp. Neurol.* 142 47-65; Bickel et al (1993) *Proc Natl. Acad. Sci. USA* 90, 2618-2622; Friden et al (1996) *J. Pharm. Exp. Ther.* 278 1491-1498, U.S. Pat. No. 5,182,107, U.S. Pat. No. 5,154,924, U.S. Pat. No. 5,833,988, U.S. Pat. No. 5,527,527). Once bound to the receptor, both components of the bispecific antibody pass across the BBB by the process of transcytosis. Alternatively the agent may be a ligand which binds such cell surface receptors e.g. insulin, transferrin or low density lipoprotein (Descamps et al (1996) *Am. J. Physiol.* 270H1149-H1158;

Duffy et al (1987) *Brain Res.* 420 32-38; Dehouck et al (1997) *J. Cell Biol.* 1997 877-889). Naturally occurring peptides such as penetratin and SynB1 and Syn B3 which are known to improve transport across the BBB can also be used (Rouselle et al (2000) *Mol. Pharm.* 57, 679-686 and Rouselle et al (2001) *Journal of Pharmacology and Experimental Therapeutics* 296, 124-131).

The term "donor antibody" refers to an antibody (monoclonal, or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal, or recombinant) heterologous to the donor antibody, which contributes all (or any portion, but preferably all) of the amino acid sequences encoding its heavy and/or light chain framework regions and/or its heavy and/or light chain constant regions to the first immunoglobulin partner. Preferably a human antibody is the acceptor antibody.

"CDRs" are defined as the complementarity determining region amino acid sequences of an antibody which are the hypervariable regions of immunoglobulin heavy and light chains. See, e.g., Kabat et al., *Sequences of Proteins of Immunological Interest,* 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence. For example, (silent) mutations can be constructed, via substitutions, when certain endonuclease restriction sites are created within or surrounding CDR-encoding regions. The present invention contemplates the use of analogs of the antibody of the invention. It is well known that minor changes in amino acid or nucleic acid sequences may lead e.g. to an allelic form of the original protein which retains substantially similar properties. Thus analogs of the antibody of the invention includes those in which the CDRs in the hypervariable region of the heavy and light chains are at least 80% homologous, preferably at least 90% homologous and more preferably at least 95% homologous to the CDRs as defined above as CDRH1, CDRH2, CDRH3, CDRL1, CDRL2 and CDRL3 and retain MAG neutralising activity. Amino acid sequences are at least 80% homologous if they have 80% identical amino acid residues in a like position when the sequences are aligned optimally, gaps or insertions being counted as non-identical residues.

Analogs may also arise as allelic variations. An "allelic variation or modification" is an alteration in the nucleic acid sequence. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore [Pharmacia] system, or other non-protein substances useful in the medical field and safe for administration to humans and animals. Other effector agents may include a macrocycle, for chelating a heavy metal atom, or radioisotopes. Such effector agents may also be useful to increase the half-life of the altered antibodies, e.g., polyethylene glycol.

A neutralising antibody specific for MAG has been described (Poltorak et al (1987) *Journal of Cell Biology* 105, 1893-1899, DeBellard et al (1996) *Mol. Cell. Neurosci.* 7, 89-101; Tang et al (1997) *Mol. Cell. Neurosci.* 9, 333-346; Torigoe K and Lundborg G (1997) *Exp. Neurology* 150, 254-262) and is commercially available (MAB1567 (Chemicon)).

Alternatively, one can construct antibodies, altered antibodies and fragments, by immunizing a non-human species (for example, bovine, ovine, monkey, chicken, rodent (e.g., murine and rat), etc.) to generate a desirable immunoglobulin upon presentation with native MAG from any species against which antibodies cross reactive with human MAG can be generated, e.g. human or chicken. Conventional hybridoma techniques are employed to provide a hybridoma cell line secreting a non-human mAb to MAG. Such hybridomas are then screened for binding using MAG coated to 384- or 96-well plates, with biotinylated MAG bound to a streptavidin coated plate. or in a homogenous europium-APC linked immunoassay using biotinylated MAG.

A native human antibody can be produced in a human antibody mouse such as the "Xenomouse" (Abgenix) where the mouse immunoglobulin genes have been removed and genes encoding the human immunoglobulins have been inserted into the mouse chromosome. The mice are immunised as normal and develop an antibody response that is derived from the human genes. Thus the mouse produces human antibodies obviating the need to humanize the after selection of positive hybridomas. (See Green L. L., *J Immunol Methods* 1999 Dec. 10; 231(1-2):11-23).

The present invention also includes the use of Fab fragments or $F(ab')_2$ fragments derived from mAbs directed against MAG. These fragments are useful as agents protective in vivo. A Fab fragment contains the entire light chain and amino terminal portion of the heavy chain; and an $F(ab')_2$ fragment is the fragment formed by two Fab fragments bound by disulfide bonds. Fab fragments and $F(ab')_2$ fragments can be obtained by conventional means, e.g., cleavage of mAb with the appropriate proteolytic enzymes, papain and/or pepsin, or by recombinant methods. The Fab and F(ab')₂ fragments are useful themselves as therapeutic or prophylactic, and as donors of sequences including the variable regions and CDR sequences useful in the formation of recombinant or humanized antibodies as described herein.

The Fab and F(ab')2 fragments can also be constructed via a combinatorial phage library (see, e.g., Winter et al., *Ann. Rev. Immunol.*, 12:433-455 (1994)) or via immunoglobulin chain shuffling (see, e.g., Marks et al., *Bio/Technology*, 10:779-783 (1992), which are both hereby incorporated by reference in their entirety.

Thus human antibody fragments (Fv, scFv, Fab) specific for MAG can be isolated using human antibody fragment phage display libraries. A library of bacteriophage particles, which display the human antibody fragment proteins, are panned against the MAG protein. Those phage displaying antibody fragments that bind the MAG are retained from the library and clonally amplified. The human antibody genes are then exicised from the specific bacteriophage and inserted into human IgG expression constructs containing the human IgG constant regions to form the intact human IgG molecule with the variable regions from the isolated bacteriophage specific for MAG.

The donor antibodies may contribute sequences, such as variable heavy and/or light chain peptide sequences, framework sequences, CDR sequences, functional fragments, and analogs thereof, and the nucleic acid sequences encoding them, useful in designing and obtaining various altered antibodies which are characterized by the antigen binding specificity of the donor antibody.

Taking into account the degeneracy of the genetic code, various coding sequences may be constructed which encode the variable heavy and light chain amino acid sequences, and CDR sequences as well as functional fragments and analogs thereof which share the antigen specificity of the donor antibody. Isolated nucleic acid sequences, or fragments thereof, encoding the variable chain peptide sequences or CDRs can be used to produce altered antibodies, e.g., chimeric or humanized antibodies, or other engineered antibodies when operatively combined with a second immunoglobulin partner.

Altered immunoglobulin molecules can encode altered antibodies which include engineered antibodies such as chimeric antibodies and humanized antibodies. A desired altered immunoglobulin coding region contains CDR-encoding regions that encode peptides having the antigen specificity of an anti-MAG antibody, preferably a high affinity antibody, inserted into a first immunoglobulin partner (a human framework or human immunoglobulin variable region).

Preferably, the first immunoglobulin partner is operatively linked to a second immunoglobulin partner. The second immunoglobulin partner is defined above, and may include a sequence encoding a second antibody region of interest, for example an Fc region. Second immunoglobulin partners may also include sequences encoding another immunoglobulin to which the light or heavy chain constant region is fused in frame or by means of a linker sequence. Engineered antibodies directed against functional fragments or analogs of MAG may be designed to elicit enhanced binding.

The second immunoglobulin partner may also be associated with effector agents as defined above, including non-protein carrier molecules, to which the second immunoglobulin partner may be operatively linked by conventional means.

Fusion or linkage between the second immunoglobulin partners, e.g., antibody sequences, and the effector agent may be by any suitable means, e.g., by conventional covalent or ionic bonds, protein fusions, or hetero-bifunctional cross-linkers, e.g., carbodiimide, glutaraldehyde, and the like. Such techniques are known in the art and readily described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art.

In still a further embodiment, the antibody of the invention may have attached to it an additional agent. For example, the procedure of recombinant DNA technology may be used to produce an engineered antibody of the invention in which the Fc fragment or CH2-CH3 domain of a complete antibody molecule has been replaced by an enzyme or other detectable molecule (i.e., a polypeptide effector or reporter molecule).

The second immunoglobulin partner may also be operatively linked to a non-immunoglobulin peptide, protein or fragment thereof heterologous to the CDR-containing sequence having the antigen specificity of anti-MAG antibody. The resulting protein may exhibit both anti-MAG antigen specificity and characteristics of the non-immunoglobulin upon expression. That fusion partner characteristic may be, e.g., a functional characteristic such as another binding or receptor domain, or a therapeutic characteristic if the fusion partner is itself a therapeutic protein, or additional antigenic characteristics.

Another desirable protein of this invention may comprise a complete antibody molecule, having full length heavy and light chains, or any discrete fragment thereof, such as the Fab or F(ab')₂ fragments, a heavy chain dimer, or any minimal recombinant fragments thereof such as an $F_v$ or a single-chain antibody (SCA) or any other molecule with the same specificity as the selected donor mAb. Such protein may be used in the form of an altered antibody, or may be used in its unfused form.

Whenever the second immunoglobulin partner is derived from an antibody different from the donor antibody, e.g., any isotype or class of immunoglobulin framework or constant regions, an engineered antibody results. Engineered antibodies can comprise immunoglobulin (Ig) constant regions and variable framework regions from one source, e.g., the acceptor antibody, and one or more (preferably all) CDRs from the donor antibody. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity.

Such engineered antibodies are designed to employ one (or both) of the variable heavy and/or light chains of the anti-MAG mAb or one or more of the heavy or light chain CDRs. The engineered antibodies may be neutralising, as above defined.

Such engineered antibodies may include a humanized antibody containing the framework regions of a selected human immunoglobulin or subtype, or a chimeric antibody containing the human heavy and light chain constant regions fused to the anti-MAG antibody functional fragments. A suitable human (or other animal) acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody.

Desirably the heterologous framework and constant regions are selected from human immunoglobulin classes and isotypes, such as IgG (subtypes 1 through 4), IgM, IgA, and IgE. However, the acceptor antibody need not comprise only human immunoglobulin protein sequences. For instance a gene may be constructed in which a DNA sequence encoding part of a human immunoglobulin chain is fused to a DNA sequence encoding a non-immunoglobulin amino acid sequence such as a polypeptide effector or reporter molecule.

Preferably, in a humanized antibody, the variable domains in both human heavy and light chains have been engineered by one or more CDR replacements. It is possible to use all six CDRs, or various combinations of less than the six CDRs. Preferably all six CDRs are replaced. It is possible to replace the CDRs only in the human heavy chain, using as light chain the unmodified light chain from the human acceptor antibody. Alternatively, a compatible light chain may be selected from another human antibody by recourse to the conventional antibody databases. The remainder of the engineered antibody may be derived from any suitable acceptor human immunoglobulin.

The engineered humanized antibody thus preferably has the structure of a natural human antibody or a fragment thereof, and possesses the combination of properties required for effective therapeutic use.

It will be understood by those skilled in the art that an engineered antibody may be further modified by changes in variable domain amino acids without necessarily affecting the specificity and high affinity of the donor antibody (i.e., an analog). It is anticipated that heavy and light chain amino acids may be substituted by other amino acids either in the variable domain frameworks or CDRs or both.

In addition, the constant region may be altered to enhance or decrease selective properties of the molecules of the instant invention. For example, dimerization, binding to Fc receptors, or the ability to bind and activate complement (see, e.g., Angal et al., *Mol. Immunol,* 30:105-108 (1993), Xu et al., *J. Biol. Chem.,* 269:3469-3474 (1994), Winter et al., EP 307, 434-B).

An altered antibody which is a chimeric antibody differs from the humanized antibodies described above by providing the entire non-human donor antibody heavy chain and light chain variable regions, including framework regions, in association with immunoglobulin constant regions from other species, preferably human for both chains.

Preferably, the variable light and/or heavy chain sequences and the CDRs of suitable donor mAbs, and their encoding nucleic acid sequences, are utilized in the construction of altered antibodies, preferably humanized antibodies, of this invention, by the following process. The same or similar techniques may also be employed to generate other embodiments of this invention.

A hybridoma producing a selected donor mAb is conventionally cloned, and the DNA of its heavy and light chain variable regions obtained by techniques known to one of skill in the art, e.g., the techniques described in Sambrook et al., (*Molecular Cloning (A Laboratory Manual)*, 2nd edition, Cold Spring Harbor Laboratory (1989)). The variable heavy and light regions containing at least the CDR-encoding regions and those portions of the acceptor mAb light and/or heavy variable domain framework regions required in order to retain donor mAb binding specificity, as well as the remaining immunoglobulin-derived parts of the antibody chain derived from a human immunoglobulin are obtained using polynucleotide primers and reverse transcriptase. The CDR-encoding regions are identified using a known database and by comparison to other antibodies.

A mouse/human chimeric antibody may then be prepared and assayed for binding ability. Such a chimeric antibody contains the entire non-human donor antibody $V_H$ and $V_L$ regions, in association with human Ig constant regions for both chains.

Homologous framework regions of a heavy chain variable region from a human antibody may be identified using computerized databases, e.g., KABAT®, and a human antibody having homology to the donor antibody will be selected as the acceptor antibody. A suitable light chain variable framework region can be designed in a similar manner.

A humanized antibody may be derived from the chimeric antibody, or preferably, made synthetically by inserting the donor mAb CDR-encoding regions from the heavy and light chains appropriately within the selected heavy and light chain framework. Alternatively, a humanized antibody can be made using standard mutagenesis techniques. Thus, the resulting humanized antibody contains human framework regions and donor mAb CDR-encoding regions. There may be subsequent manipulation of framework residues. The resulting humanized antibody can be expressed in recombinant host cells, e.g., COS, CHO or myeloma cells.

A conventional expression vector or recombinant plasmid is produced by placing these coding sequences for the antibody in operative association with conventional regulatory control sequences capable of controlling the replication and expression in, and/or secretion from, a host cell. Regulatory sequences include promoter sequences, e.g., CMV promoter, and signal sequences, which can be derived from other known antibodies. Similarly, a second expression vector can be produced having a DNA sequence which encodes a complementary antibody light or heavy chain. Preferably this second expression vector is identical to the first except insofar as the coding sequences and selectable markers are concerned, so to ensure as far as possible that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The humanized antibody which includes the association of both the recombinant heavy chain and/or light chain is screened from culture by appropriate assay, such as ELISA or RIA. Similar conventional techniques may be employed to construct other altered antibodies and molecules.

Suitable vectors for the cloning and subcloning steps employed in the methods and construction of the compositions of this invention may be selected by one of skill in the art. For example, the conventional pUC series of cloning vectors, may be used. One vector, pUC19, is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

Similarly, the vectors employed for expression of the antibodies may be selected by one of skill in the art from any conventional vector. The vectors also contain selected regulatory sequences (such as CMV promoters) which direct the replication and expression of heterologous DNA sequences in selected host cells. These vectors contain the above described DNA sequences which code for the antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antibodies or altered immunoglobulin molecules thereof. Host cells useful for the cloning and other manipulations of these cloning vectors are also conventional. However, most desirably, cells from various strains of *E. coli* are used for replication of the cloning vectors and other steps in the construction of altered antibodies of this invention.

Suitable host cells or cell lines for the expression of the antibody of the invention are preferably mammalian cells such as NS0, Sp2/0, CHO, COS, a fibroblast cell (e.g., 3T3), and myeloma cells, and more preferably a CHO or a myeloma cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs of the present invention (see, e.g., Plückthun, A., *Immunol. Rev.*, 130:151-188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host. For example, various strains of *E. coli* used for expression are well-known as host cells in the field of biotechnology. Various strains of *B. subtilis*, *Streptomyces*, other bacilli and the like may also be employed in this method.

Where desired, strains of yeast cells known to those skilled in the art are also available as host cells, as well as insect cells, e.g. *Drosophila* and Lepidoptera and viral expression systems. See, e.g. Miller et al., *Genetic Engineering*, 8:277-298, Plenum Press (1986) and references cited therein.

The general methods by which the vectors may be constructed, the transfection methods required to produce the host cells of the invention, and culture methods necessary to produce the altered antibody of the invention from such host cell are all conventional techniques. Likewise, once produced, the antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention. For example, preparation of altered antibodies are described in WO 99/58679 and WO 96/16990.

Yet another method of expression of the antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

Once expressed by the desired method, the antibody is then examined for in vitro activity by use of an appropriate assay. Presently conventional ELISA assay formats are employed to assess qualitative and quantitative binding of the antibody to MAG. Additionally, other in vitro assays may also be used to verify neutralizing efficacy prior to subsequent human clinical studies performed to evaluate the persistence of the antibody in the body despite the usual clearance mechanisms.

The therapeutic agents of this invention may be administered as a prophylactic or post injury, or as otherwise needed. The dose and duration of treatment relates to the relative duration of the molecules of the present invention in the human circulation, and can be adjusted by one of skill in the art depending upon the condition being treated and the general health of the patient.

The mode of administration of the therapeutic agent of the invention may be any suitable route which delivers the agent to the host. The antagonists and antibodies, and pharmaceutical compositions of the invention are particularly useful for parenteral administration, i.e., subcutaneously, intramuscularly, intravenously, or intranasally.

Therapeutic agents of the invention may be prepared as pharmaceutical compositions containing an effective amount of the antagonist or antibody of the invention as an active ingredient in a pharmaceutically acceptable carrier. In the prophylactic agent of the invention, an aqueous suspension or solution containing the engineered antibody, preferably buffered at physiological pH, in a form ready for injection is preferred. The compositions for parenteral administration will commonly comprise a solution of the antagonist or antibody of the invention or a cocktail thereof dissolved in an pharmaceutically acceptable carrier, preferably an aqueous carrier. A variety of aqueous carriers may be employed, e.g., 0.9% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antagonist or antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an antagonist or antibody of the invention. Similarly, a pharmaceutical composition of the invention for intravenous infusion could be made up to contain about 250 ml of sterile Ringer's solution, and about 1 to about 30 and preferably 5 mg to about 25 mg of an engineered antibody of the invention. Actual methods for preparing parenterally administrable compositions are well known or will be apparent to those skilled in the art and are described in more detail in, for example, Remington's Pharmaceutical Science, 15th ed., Mack Publishing Company, Easton, Pa.

It is preferred that the therapeutic agent of the invention, when in a pharmaceutical preparation, be present in unit dose forms. The appropriate therapeutically effective dose can be determined readily by those of skill in the art. To effectively treat stroke and other neurological diseases in a human, one dose of up to 700 mg per 70 kg body weight of an antagonist or antibody of this invention should be administered parenterally, preferably i.v. or i.m. (intramuscularly). Such dose may, if necessary, be repeated at appropriate time intervals selected as appropriate by a physician.

The antibodies described herein can be lyophilized for storage and reconstituted in a suitable carrier prior to use. This technique has been shown to be effective with conventional immunoglobulins and art-known lyophilization and reconstitution techniques can be employed.

In another aspect, the invention provides a pharmaceutical composition comprising anti-MAG antibody or a functional fragment thereof and a pharmaceutically acceptable carrier for use in the promotion of oligodendrocyte survival.

The following examples illustrate the invention.

Example 1

Anti-MAG monoclonal antibody, control mouse IgG1 and Tau 1 were purchased from Chemicon. A Western blot of rat tissues lysates, prepared under non-reducing conditions was purchased from Chemicon.

Cultures of primary oligodendrocytes were prepared from $O_2A$ progenitor cells isolated from P0-P2 Sprague-Dawley rat as described (Vinson et al, Mol. Cell. Neurosci. Vol 22 2003) and differentiated in culture for 5 days at which point they extended out myelin-like membranes positive for myelin markers and expressed MAG at the cell surface (Vinson et al, Mol. Cell. Neurosci. Vol 22 2003).

For survival assays, $O_2A$ cells were seeded in 48-well plates ($5\times10^4$ per well) in 500 µl Sato's medium (400 ng/ml T3, 400 ng/ml T4, 2 mM glutamine, 50 U/ml penicillin and 50 µg/ml streptomycin, 5 ml N2 supplement (Life Technology) with 0.5% FCS and were used at 5 days in vitro. Glutamate and antibodies were diluted in cystine-free DMEM, and cystine in 1N HCl. All incubations were performed at 37° C. for 16 hr. Cell survival was quantified by colorimetric MTT assay (Skaper et al 1990, P M Conn (Ed.), Methods in Neurosciences Vol. 2 p 17-33, Academic Press). Absorbance was measured at 570 and 630 nm with a micro-ELISA spectrophotometer.

Immunohistochemistry

Immunohistochemistry was conducted using standard procedures as described previously (Irving et al. 2001 Acta Neuropathol (Berl) 102, 627-35. Incubation with the primary antibody was conducted (Tau 1 1:500, Egr-1 1:200) overnight at 4° C. Using analySIS® imaging system software, the number of egr-1 positive nuclei were counted per 25 µm² area. Twelve areas were measured from the contralateral and ipsilateral: striatum, hind limb cortex and cingulate cortex in two separate sections per animal (n=6/group). Operator was blinded to treatment groups.

The anti-MAG antibody was utilised to examine the effect of engagement of cell surface MAG on the protection of oligodendrocytes from glutamate mediated cell death. $O_2A$ oligodendrocyte precursor cells were differentiated in vitro for 6 days. At this time, like adult rat brain, they expressed both long and short isoforms of MAG at the RNA level and stained positive for MAG at the cell surface and (Vinson et al, 2003). Treatment with 2 mM glutamate in cystine-free medium for 16 hours, reduced cell viability by 50% (FIG. 1). Death was not rescued by addition of NMDA receptor antagonist MK801 or AMPA receptor antagonist DNQX (data not shown) but was completely reversed by the addition of exogenous cystine (FIG. 1). Addition of anti-MAG antibody, but not control IgG reduced the degree of cell death, with maximum protection seen at 1 µg/ml (FIG. 1).

Figure 2:
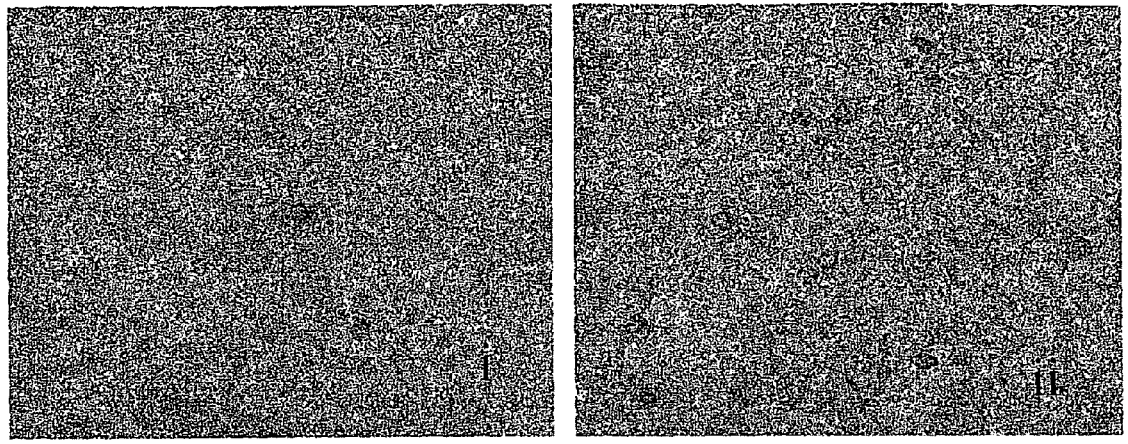
FIG. 2: Oligodendrocytes present in ischaemic lesion with and without anti-MAG antibody.

WO 02/062383 demonstrates in a rat model of stroke that administration of an anti-MAG antibody results in an improvement in functional recovery which was accompanied by a marked reduction in lesion area measured seven days following transient MCAO. Animals treated with anti-MAG antibody showed reduced neuronal loss (approximately 40-50%) as detected by CFV staining and reduced damage to axonal tracts as delineated by Tau 1 immunostaining compared to IgG treated controls. Tau 1 immunostaining in oligodendrocytes is thought to be indicative of cellular integrity post-stroke (Irving et al, Acta Neuropathol. (Berl), 102, p 627-35, 2001). Tau1 is increased in oligodendroytes up to 24 h following MCAO in the ischaemic hemisphere (Irving et al, J. Cereb. Blood Flow Metab. 17, p 612-22, 1997, Valeriani et al, J. Cereb. Blood Flow Metab. 20 P 765-771, 2000), but is lost as the white matter degenerates at 1 week following MCAO (Irving et al, Acta Neuropathol. (Berl) 102, p 627-35, 2001). The number of Tau 1 positive, histologically normal, oligodendrocytes present within the ischaemic lesion was greater following anti-MAG antibody compared to FIG. 2 without administration. The ability of the anti-MAG antibody to prevent Tau 1 loss in oligodendrocytes within the lesion area suggests that treatment may have maintained a degree of oligodendrocyte integrity.

Example 2

Chimeric Antibody

Seq ID No 7 provides the amino acid sequence of a chimeric immunoglobulin heavy chain in which the murine anti-MAG heavy chain variable region is associated with a functional immunoglobulin secretion signal sequence, and with an altered form of the human IgG1 constant region, in which Kabat residues 248 and 250 have been mutated to alanine in order to disable the effector functions of binding to FcγRI and complement protein C1q (Duncan, A. R. and Winter, G. Localization of the C1q binding site on antibodies by surface scanning. Nature 332, 738-740, 1988. Duncan, A. R., Woolf, J. M., Partridge, L. J., Burton, D. R. and Winter, G. Localisation of the binding site for human FcR1 on IgG. Nature 332, 563-564, 1988). Such mutations are optionally made in order to customise the properties of an altered antibody to achieve a particular therapeutic effect—for example binding to and blocking the function of an antigen without activating lytic effector mechanisms.

(Seq ID No 7)
MGWSCIILFLVATATGVHSEIQLVQSGPELKKPGETNKISCKASGYTFTN

YGMNWVKQAPGKGLKWMGWINTYTGEPTYADDFTGRFAFSLETSASTAYL

QISNLKNEDTATYFCARNPINYYGINYEGYVMDYWGQGTLVTVSSASTKG

PSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDK

THTCPPCPAPELAGAPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNV

FSCSVMHEALHNHYTQKSLSLSPGK

Seq ID No 8 provides the amino acid sequence of a chimeric immunoglobulin light chain in which the murine anti-MAG light chain variable region is associated with a functional immunoglobulin secretion signal sequence, and with the human kappa constant region.

(Seq ID No 8)
MGWSCIILFLVATATGVHSNIMMTQSPSSLAVSAGEKVTMSCKSSHSVLY

SSNQKNYLAWYQQKPGQSPKLLIYWASTRESGVPDRFTGSGSGTDFTLTI

INVHTEDLAVYYCHQYLSSLTFGTGTKLEIKRTVAAPSVFIFPPSDEQLK

SGTASVVCLLNNFYPREAKVQWKVDNALQSGNSQESVTEQDSKDSTYSLS

STLTLSKADYEKHKVYACEVTHQGLSSPVTKSFNRGEC

Similarly, the anti-MAG variable regions may be associated with immunoglobulin constant regions which lack mutations disabling effector functions. Seq ID No 9 the amino acid sequence of a chimeric immunoglobulin heavy chain in which the murine anti-MAG heavy chain variable region is associated with a functional immunoglobulin secretion signal sequence, and with a wild-type form of the human IgG1 constant region.

(Seq ID No 9)
MGWSCIILFLVATATGVHSEIQLVQSGPELKKPGETNKISCKASGYTFTN

YGMNWVKQAPGKGLKWMGWINTYTGEPTYADDFTGRFAFSLETSASTAYL

QISNLKNEDTATYFCARNPINYYGINYEGYVMDYWGQGTLVTVSSASTKG

PSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDK

THTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNV

FSCSVMHEALHNHYTQKSLSLSPGK

From the information provided in Seq ID Nos 7, 8 and 9, cDNA inserts encoding these chimeric chains may be prepared by standard molecular biology techniques well known to those skilled in the art. Briefly, the genetic code is used to identify nucleotide codons encoding the desired amino acids, creating a virtual cDNA sequence encoding the chimeric protein. If the cDNA insert is desired to be expressed in a particular organism, then particularly favoured codons may be selected according to known codon usage biases. The desired nucleotide sequence is then synthesised by means of PCR amplification of a template comprising overlapping synthetic oligonucleotides which, as a contig, represent the desired sequence. The resulting product may also be modified by PCR or mutagenesis to attach restriction sites to facilitate cloning into a suitable plasmid for expression or further manipulations.

Example 3

Chimeric Antibody Binds to Rat MAG in ELISA

Figure 3:
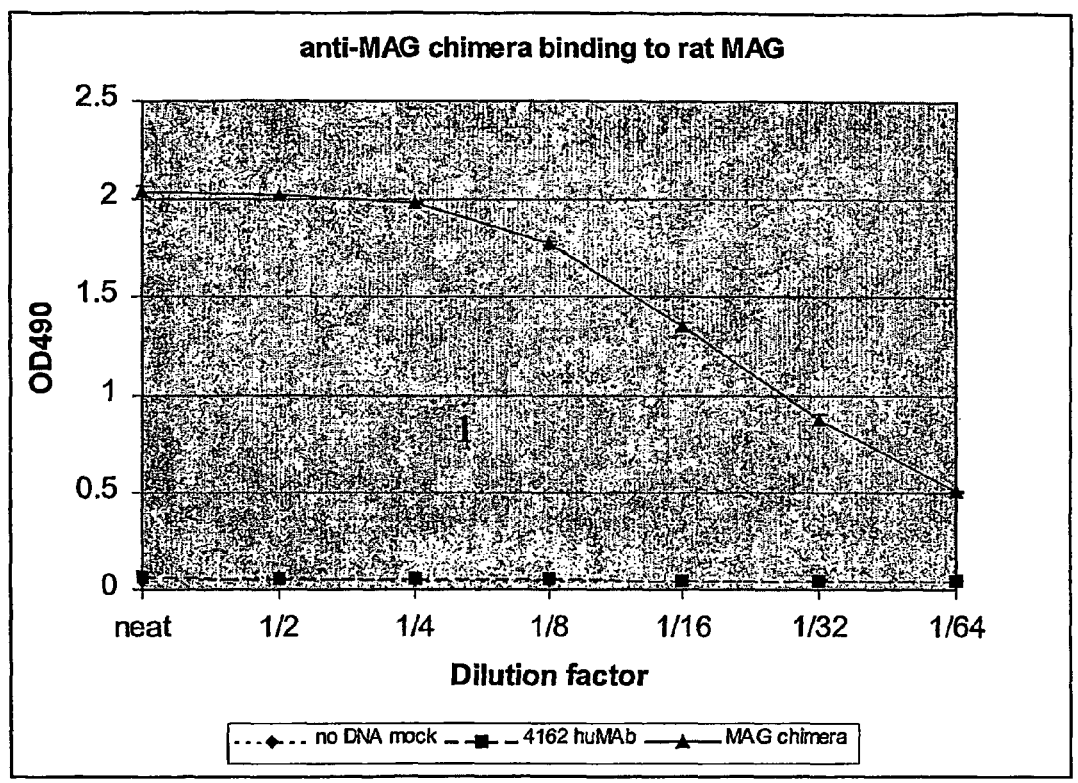
FIG. 3: Anti-MAG chimera binding to rat MAG.

Chimeric anti-MAG antibody containing the light and heavy chain CDRs of the invention was produced by transient transfection of CHO cells. Antibody concentration was determined by ELISA and estimated to be around 0.5 µg/ml. For MAG binding, commercially available ratMAG-Fc was used. Due to the fusion with human Fc bound chimeric antibodies could not be detected using anti-human IgG secondary antibodies. Instead, anti-human kappa light chain-specific antibody was used. FIG. 3 shows that this chimeric antibody binds to MAG even at 1/64 dilution. An unrelated humanised antibody and culture supernatant from mock transfected cells did not generate any signal in this assay.

Procedure:

ELISA microtiter plates (Nunc Maxisorp) were coated with 1 µg/ml rat MAG-Fc fusion protein (R&D systems; 538-MG) in PBS at 4° C. overnight. Plates were washed twice with PBS and then blocked with PBS/BSA (1% w/v) for 1 h at room temperature (RT). Culture supernatants from transiently transfected CHO cells were passed through 0.2 µm filters and serial diluted in PBS/BSA starting at neat supernatant to 1/64 dilution. Sample dilutions were left at RT for 1 h. Plates were then washed three times with PBS/Tween 20 (0.1%). Detection antibody was goat anti-human kappa light chain specific-peroxidase conjugate (Sigma A-7164) diluted at 1/2000 in PBS/BSA. The detection antibody was incubated for 1 h at RT and the plates washed as above. Substrate solution (Sigma Fast OPD P-9187) was added and incubated until appropriate colour development was detected and then stopped using 3M $H_2SO_4$. Colour development was read at 490 nm.

Example 4

Humanised Antibodies

Altered antibodies include humanised antibodies which comprise humanised variable regions linked to human constant regions. Examples of humanised anti-MAG immunoglobulin chains of the invention are provided in FIG. 4. Humanised antibodies using human IgG1, IgG2, IgG3, IgG4, IgA, IgE, IgM, IgD constant regions may be produced.

FIG. 4 (Seq ID No: 18) provides an example of the amino acid sequence of a humanised immunoglobulin heavy chain in which the humanised anti-MAG heavy chain variable region is associated with a functional immunoglobulin secretion signal sequence, and with an altered form of the human IgG1 constant region, in which Kabat residues 248 and 250 have been mutated to alanine in order to disable the effector functions of binding to FcγRI and complement protein C1q (Duncan, A. R. and Winter, G. Localization of the C1q binding site on antibodies by surface scanning. Nature 332, 738-740, 1988. Duncan, A. R., Woolf, J. M., Partridge, L. J., Burton, D. R. and Winter, G. Localisation of the binding site for human FcR1 on IgG. Nature 332, 563-564, 1988). Such mutations are optionally made in order to customise the properties of an altered antibody to achieve a particular therapeutic effect—for example binding to and blocking the function of an antigen without activating lytic effector mechanisms.

FIG. 4 (Seq ID No. 19) also provides an example of the amino acid sequence of a humanised immunoglobulin light chain in which the humanised anti-MAG light chain variable region is associated with a functional immunoglobulin secretion signal sequence, and with the human kappa constant region.

Similarly, the anti-MAG variable regions may be associated with immunoglobulin constant regions which lack mutations disabling effector functions. FIG. 4 (Seq ID No. 20) provides the amino acid sequence of a humanised immunoglobulin heavy chain in which the humanised anti-MAG heavy chain variable region is associated with a functional immunoglobulin secretion signal sequence, and with a wild-type form of the human IgG1 constant region.

From the information provided in FIG. 4, cDNA inserts encoding these humanised chains may be prepared by standard molecular biology techniques well known to those skilled in the art. Briefly, the genetic code is used to identify nucleotide codons encoding the desired amino acids, creating a virtual cDNA sequence encoding the protein. If the cDNA insert is desired to be expressed in a particular organism, then particularly favoured codons may be selected according to known codon usage biases. The desired nucleotide sequence is then synthesised by means of PCR amplification of a template comprising overlapping synthetic oligonucleotides which, as a contig, represent the desired sequence. The resulting product may also be modified by PCR or mutagenesis to attach restriction sites to facilitate cloning into a suitable plasmid for expression or further manipulations.

Example 5

Humanised Anti-MAG Antibodies Bind to Rat and Human MAG in Elisa

1) Direct Binding ELISA to Rat MAG-Fc Fusion Protein of Normalised Amounts of Culture Supernatant for 9 Humanised Heavy and Light Chain Combinations Humanised anti-MAG antibodies containing the light and heavy chain CDRs of the invention were produced by transient transfection of CHO cells. For this, Transfast transfection reagent (Promega; E2431) was used and transfections carried out according to manufactures instructions. In brief, ~10⁶ CHO cells were plated out per well of 6-well culture plates. The following day mammalian expression vector DNA encoding the appropriate heavy or light chain were mixed at 1:1 ratio (5 µg total DNA) in medium (Optimem1 with Glutamax; Gibco #51985-026). Transfast transfection reagent was added and the solution transferred to wells with confluent cell layers. After 1 h at 37° C. in the cell incubator, the DNA/Transfast mixture was overlaid with 2 ml Optimem medium and left for 48-72 h in the incubator. Supernatants were harvested, cleared by centrifugation and passed through 0.2 µm filters. 9 heavy and light variable chain combinations were produced from the sequences shown in the table below and the IgG1 heavy chain constant regions were functional according to Seq.ID.

| Seq ID No (V-regions) | Description | Alternative name |
|---|---|---|
| 10 | Humanised Vh | BVh1 |
| 11 | Humanised Vh | BVh2 |
| 12 | Humanised Vh | BVh3 |
| 14 | Humanised Vl | CVl1 |
| 15 | Humanised Vl | CVl2 |
| 16 | Humanised Vl | CVl3 |
| 17 | Humanised Vl | CVl4 |

Figure 5:
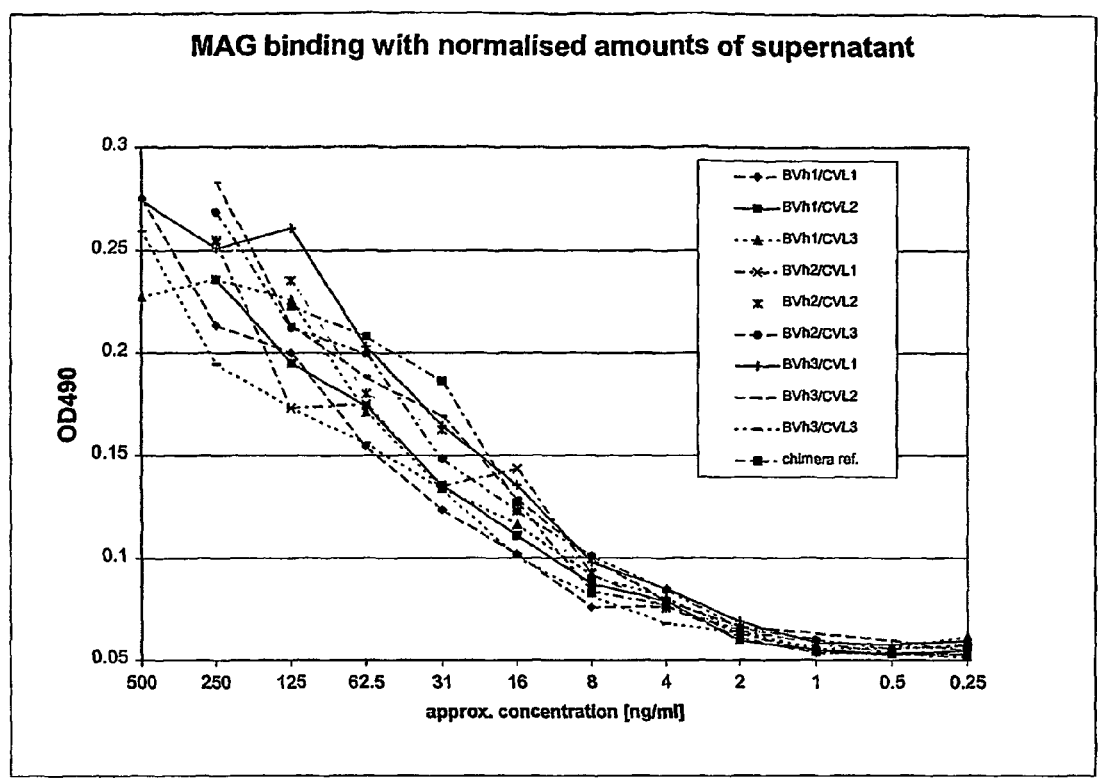
FIG. 5: Humanised anti-MAG antibodies bind to rat MAG

Antibody concentration was determined by ELISA and the amounts of supernatant used in the assay normalised to a starting concentration of 250 or 500 ng/ml (depending on concentration of culture supernatant). As antigen, commercially available ratMAG-Fc was used (R&D Systems; 538-MG). Due to the fusion of this antigen with human Fc, bound chimeric antibodies could not be detected using general anti-human IgG secondary antibodies. Instead, anti-human kappa light chain-specific antibody was used. FIG. 5 shows that all 9 humanised antibodies examined here bound to rat MAG with very similar binding curves down to ~4 ng/ml. The chimeric antibody used as a reference showed binding characteristics that fell within the group of humanised antibodies examined here. Although not absolute, this may suggest that the affinities of the humanised antibodies examined here lie very closely within the affinity range of the non-humanised chimeric antibody used as a reference here.

Procedure 96-well Nunc Maxisorp plates were coated overnight at 4° C. with rat MAG-Fc fusion protein (1 µg/ml; R&D Systems; Cat. No. 538-MG) in PBS. Plates were washed twice with PBS containing Tween20 (0.1% v/v; PBST) and blocked with PBS containing BSA (1% w/v) for 1 h at room temperature (RT). Variable amounts of culture supernatants were serial diluted in blocking buffer and added to the blocked wells starting at approximately 500 or 250 ng/ml. Antibody concentrations of supernatants were based on independent assays measuring the amount of humanised antibody present in each culture supernatant. Chimeric mouse-human (non-humanised) antibody was also included as reference. Antibody samples were incubated 1 h at RT and plates then washed 3× with PBST. Secondary antibody (Goat anti-human light chain specific-peroxidase conjugate; Sigma A-7164) was added diluted 1/5000 in blocking buffer and incubated for 1 h at RT. Wells were washed three times as above and binding detected by adding substrate (OPD tablets dissolved according to instructions; Sigma P-9187). Colour development was monitored and the reaction stopped using 3M $H_2SO_4$. Colour development was read at 490 nm.

Figure 6:
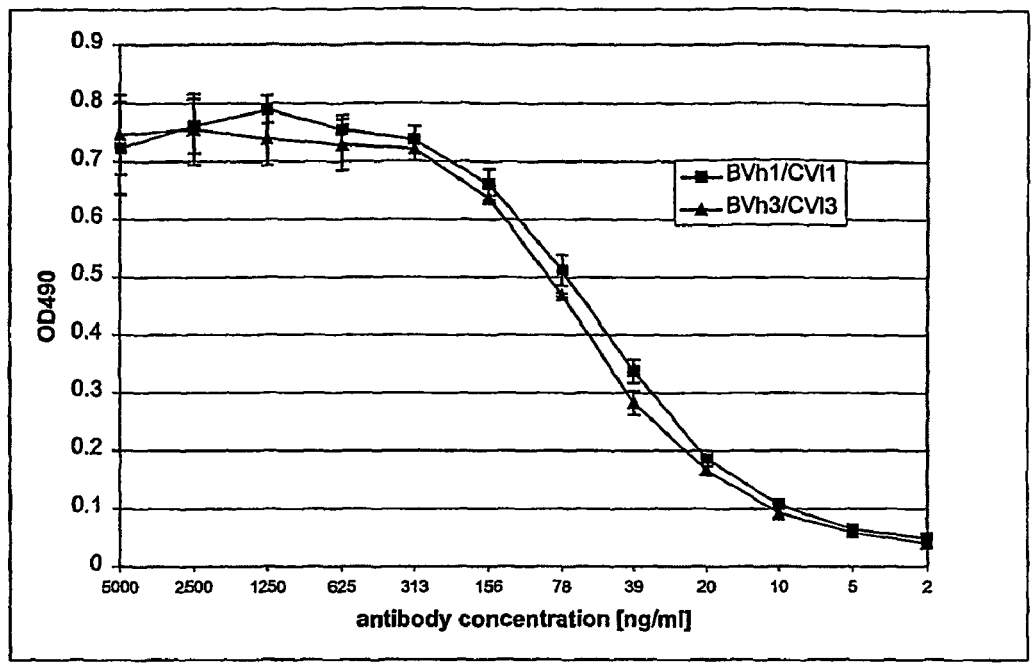
FIG. 6: Purified humanised anti-MAG antibodies bind to rat MAG

2) Direct Binding ELISA to Rat MAG-Fc Fusion Protein of Two Purified Humanised Anti-MAG Antibody Heavy-Light Chain Combinations Two humanised antibodies consisting of heavy and light chain variable region combinations BVh1/CVl1 and BVh3/CVl3 (table FIG. 4) and a mutated IgG1 constant region as exemplified by SEQ.I.D.NO:30 (which is BVh1/CVl1 mutated IgG1, those skilled in the art can readily derive the sequence for the BVh3/CVl3 equivalent) were produced by a scaled-up version of the transient transfection described in example 3 and purified using protein A affinity chromatography. Purified antibody material was dialysed against PBS and the concentration determined by OD280 reading. Antibody concentrations were adjusted to 5000 ng/ml and used as serial dilutions in a rat MAG-Fc binding ELISA. FIG. 6 shows that purified antibody material binds rat MAG-Fc and that both heavy and light chain variable region combinations tested here are extremely similar.

Method:

96-well Nunc Maxisorp plates were coated overnight at 4° C. with rat MAG-Fc fusion protein (2.5 µg/ml; R&D Systems; Cat. No. 538-MG) in PBS. Plates were washed twice with PBS containing Tween20 (0.1% v/v; PBST) and blocked with PBS containing BSA (1% w/v) for 1 h at room temperature (RT). Purified humanised antibody was adjusted to a starting concentration of 5 µg/ml in blocking buffer and then serial diluted. Antibody samples were incubated 1 h at RT and plates then washed 3× with PBST. Secondary antibody (Goat anti-human light chain specific-peroxidase conjugate; Sigma A-7164) was added diluted ⅕₀₀₀ in blocking buffer and incubated for 1 h at RT. Wells were washed three times as above and binding detected by adding substrate (OPD tablets dissolved according to instructions; Sigma P-9187). Colour development was monitored and the reaction stopped using 3M $H_2SO_4$. Colour development was read at 490 nm.

Results:

Both purified humanised antibodies carrying none or several framework mutations show extremely similar binding to rat MAG. The results are seen in FIG. 6.

3) Binding to Human MAG Expressed on CHO Cells of Normalised Amounts of Culture Supernatant for Two Humanised Heavy and Light Chain Combinations The same humanised variable heavy and light chain combinations described in example 5 2) were tested as cleared culture supernatants against human MAG expressed on the surface of CHO cells. The amount of culture supernatant used for each antibody was normalised based on antibody concentrations determined by ELISA. For this, 96-well plates (Nunc Maxisorp) were coated overnight at 4° C. with goat anti-human IgG (gamma) chain (Sigma 1-3382; in bicarbonate buffer pH9.6; 2 µg/ml). Following day, plates were washed twice with wash buffer (PBST) and blocked by adding at least 7511 blocking buffer (PBS containing BSA 1% w/v) for 1 h at RT. Antibody sample solution were serial diluted in blocking buffer (starting dilution neat or ½) in duplicate. Ab standard was purified humanised IgG1 antibody of an unrelated specificity and known concentration. The standard solution was also serial diluted across plate starting at 500 ng/ml. All antibody solutions were incubated for 1 h at RT. Plates were washed 3× as above and then incubated with goat anti-human light (kappa) chain specific (free and bound) peroxidase conjugate (Sigma; A-7164) at ⅕₀₀₀ in blocking buffer for 1 h @ RT. Plates were again washed 3× as above and incubated with substrate solution (OPD tablets; Sigma P-9187 until strong colour development. Colour development was stopped by adding 25 µl 3M H2SO4 and the plate read at 490 nm.

Figure 7:
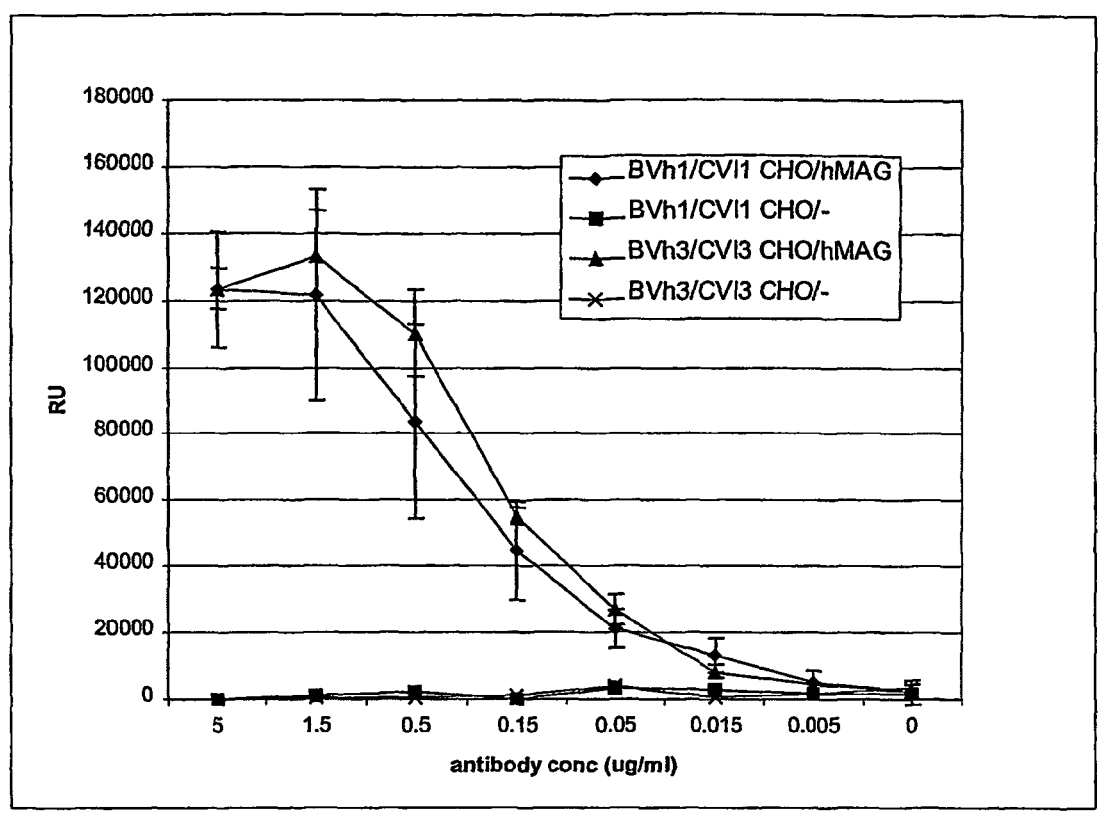
FIG. 7: Humanised anti-MAG antibodies bind to human MAG

FIG. 7 shows that both antibodies tested here are recognising human MAG and are very similar in their binding characteristics. CHO/− are negative controls of CHO cells with no MAG expressed.

Method for Eu Cell-Based ELISA 96-well plates (Costar 3595) were filled with 100 µl cell suspension/well (see table below for recommended cell number for performing assay on days 1, 2, 3 or 4).

| Day | cell number/ml |
|---|---|
| 1 | $3 \times 10^5$ |
| 2 | $1 \times 10^5$ |
| 3 | $5 \times 10^4$ |
| 4 | $1 \times 10^4$ |

Culture medium was removed and plates blocked with DMEM/F12 (Sigma D6421) containing FCS (10%), BSA (1%), NaN3 (1%; blocking buffer) for 1 hour at RT. Blocking solution was then removed and sample added (in blocking buffer 50 µl/well). Incubated samples at 4° C. for 1 h. Plates were then washed 3× with PBS using a Skatron plate washer. After wash, cells were fixed with 0.5% paraformaldehyde (diluted in PBS) for 20 minutes at 4° C. and again washed as above. 50 µl/well Europium-conjugated secondary antibody diluted in Europium buffer (50 mM Tris base, 150 mM NaCl, 0.5% BSA, 0.1 g/l, Tween 20, 7.86 mg/l DTPA at pH 7.3) was added and incubated for 1 h at 4° C.

Washed plates as above and added 2001 Delphia enhancement solution/well. Incubated solution at RT for 5-10 minutes. Wells were read within 24 hours on a Victor.

4) Competition ELISA for Binding to Rat MAG-Fc Fusion Protein of Two Purified Humanised Antibodies and the Non-Humanised Mouse Monoclonal Antibody Method:

96-well Nunc Maxisorp plates were coated overnight at 4° C. with rat MAG-Fc fusion protein (2.5 µg/ml; R&D Systems; Cat. No. 538-MG) in PBS. Plates were washed twice with PBS containing Tween20 (0.1% v/v; PBST) and blocked with PBS containing BSA (1% w/v) for 1 h at room temperature (RT). Purified humanised antibody was adjusted to a concentration of 200 ng/ml and mixed at equal volume with competitor molecules made up in blocking buffer ranging from 6000 to 0 ng/ml. Competitors were either parental mouse monoclonal antibody (anti-MAG) or an unrelated mouse monoclonal antibody (INN1) at the same concentrations (BVh1/CVl1 only). Antibody/competitor solutions were incubated 1 h at RT and plates then washed 3× with PBST. Secondary antibody (Goat anti-human light chain specific-peroxidase conjugate; Sigma A-7164) was added diluted ⅕₀₀₀ in blocking buffer and incubated for 1 h at RT. Wells were washed three times as above and binding detected by adding substrate (OPD tablets dissolved according to instructions; Sigma P-9187). Colour development was measured at 490 nm.

Results:

Both purified antibody preparations are equally competed by the original mouse monoclonal antibody but not by a mouse monoclonal antibody that has an unrelated specificity—see FIG. 8. This shows that the original mouse monoclonal antibody and the humanised antibodies tested here are probably recognising the same epitope and possibly have very similar affinities to rat MAG.

What is claimed is:

1. A method of promoting oligodendrocyte survival in a human suffering from stroke, which comprises administering to said human a therapeutically effective amount of an altered anti-myelin associated glycoprotein (anti-MAG) antibody or functional fragment thereof, wherein the altered antibody or functional fragment thereof binds to MAG and comprises:
   a heavy chain variable domain ($V_H$) which comprises in sequence hypervariable regions CDRH1 (SEQ ID NO: 4), CDRH2 (SEQ ID NO: 5), and CDRH3 (SEQ ID NO: 6) and
   a light chain variable domain ($V_L$) which comprises in sequence hypervariable regions CDRL1 (SEQ ID NO: 1), CDRL2 (SEQ ID NO: 2), and CDRL3 (SEQ ID NO: 3).

2. A method according to claim 1, wherein the altered anti-MAG antibody or functional fragment thereof comprises at least one variable domain selected from the group consisting of: a heavy chain with an amino acid sequence comprising SEQ ID NO: 7, a heavy chain with an amino acid sequence comprising SEQ ID NO: 9, and a light chain with an amino acid sequence comprising SEQ ID NO:8.

3. A method according to claim 1, wherein the altered anti-MAG antibody or functional fragment thereof comprises at least one heavy chain variable region selected from the group consisting of: SEQ ID NO: 10, SEQ ID NO: 11, SEQ ID NO: 12, and SEQ ID NO: 13 and a light chain variable region selected from the group consisting of: SEQ ID NO: 14, SEQ ID NO: 15, SEQ ID NO: 16, and SEQ ID NO: 17.

4. A method according to claim 3, wherein the altered anti-MAG antibody or functional fragment thereof comprises a heavy chain variable region comprising SEQ ID NO: 10 and a light chain variable region comprising a sequence selected from the group consisting of: SEQ ID NO: 14, SEQ ID NO: 15, SEQ ID NO: 16, and SEQ ID NO: 17.

5. A method according to claim 3, wherein the altered anti-MAG antibody or functional fragment thereof comprises a heavy chain variable region comprising SEQ ID NO: 11 and a light chain variable region comprising a sequence selected from the group consisting of: SEQ ID NO: 14, SEQ ID NO: 15, SEQ ID NO: 16, and SEQ ID NO: 17.

6. A method according to claim 3, wherein the altered anti-MAG antibody or functional fragment thereof comprises a heavy chain variable region comprising SEQ ID NO: 12 and a light chain variable region comprising a sequence selected from the group consisting of: SEQ ID NO: 14, SEQ ID NO: 15, SEQ ID NO: 16, and SEQ ID NO: 17.

7. A method according to claim 3, wherein the altered anti-MAG antibody is a humanized antibody and comprises:

(a) a heavy chain variable region comprising a sequence selected from the group consisting of: SEQ ID NO: 10, SEQ ID NO: 11, and SEQ ID NO: 12,
(b) a constant part of a human heavy chain or fragment thereof,
(c) a light chain variable region comprising a sequence selected from the group consisting of: SEQ ID NO: 14, SEQ ID NO: 15, SEQ ID NO: 16, and SEQ ID NO: 17, and
(d) a constant part of a human light chain.

8. A method according to claim 7, wherein the humanized antibody is class IgG.

9. A method according to claim 8, wherein the humanized antibody is class IgG1.

* * * * *